(12) United States Patent
Chowdhury

(10) Patent No.: US 9,642,821 B2
(45) Date of Patent: May 9, 2017

(54) MIR-182 IN THE DIAGNOSIS AND TREATMENT OF CANCER

(75) Inventor: Dipanjan Chowdhury, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/005,899

(22) Filed: Jan. 13, 2011

(65) Prior Publication Data

US 2011/0178163 A1 Jul. 21, 2011

Related U.S. Application Data

(60) Provisional application No. 61/294,946, filed on Jan. 14, 2010.

(51) Int. Cl.

| | | |
|---|---|---|
| A61K 31/166 | (2006.01) | |
| A61K 31/4184 | (2006.01) | |
| A61K 31/435 | (2006.01) | |
| A61K 31/502 | (2006.01) | |
| A61K 31/55 | (2006.01) | |
| A61K 31/7088 | (2006.01) | |
| C12Q 1/68 | (2006.01) | |

(52) U.S. Cl.
CPC ........ *A61K 31/166* (2013.01); *A61K 31/4184* (2013.01); *A61K 31/435* (2013.01); *A61K 31/502* (2013.01); *A61K 31/55* (2013.01); *A61K 31/7088* (2013.01); *C12Q 1/6886* (2013.01); *C12Q 2600/106* (2013.01); *C12Q 2600/112* (2013.01); *C12Q 2600/118* (2013.01); *C12Q 2600/178* (2013.01)

(58) Field of Classification Search
CPC combination set(s) only.
See application file for complete search history.

(56) References Cited

U.S. PATENT DOCUMENTS

2008/0293795 A1* 11/2008 Donawho .......... A61K 31/4184
514/394

OTHER PUBLICATIONS

Liu, et al. (2004) An oligonucleotide microchip for genome-wide microRNA profiling in human and mouse tissues. PNAS, v.101(26):9740-4.*
Iorio, et al. (2005) MicroRNA Gene Expression Deregulation in Human Breast Cancer. Cancer Research, v.65(16):7065-70.*
Cameron, et al. (2002). British J. Cancer, v.87:1365-9.*
Citron, et al. JCO Apr. 15, 2003 vol. 21 No. 8 1431-1439.*
Guttilla, et al. (2009) JBC, v.284(35):23204-16.*
Tacar, et al. (2012) Doxorubicin: an update on anticancer molecular action, toxicity and novel drug delivery systems. Journal of Pharmacy and Pharmacology, v.65:157-70.*
Urbanek, et al. (2015) Small RNA Detection by in Situ Hybridization Methods. International Journal of Molecular Sciences, v.16:13259-86.*
Ambros, V. "The functions of animals microRNAs", Nature, vol. 431, (2004), pp. 350-355.

Atchley, D. P. et al., "Clinical and Pathological Characteristics of Patients With *BRCA*-Positive and *BRCA*-Negative Breast Cancer", Journal of Clinical Oncology, vol. 26, No. 26, (2008), pp. 4282-4288.
Baldassarre, G. et al., "Negative Regulation of *BRCA1* Gene Expression by HMGA1 Proteins Accounts for the Reduced BRCA1 Protein Levels in Sporadic Breast Carcinoma", Molecular and Cellular Biology, vol. 23, No. 7, (2003), pp. 2225-2238.
Bandrés, E. et al., "Identification by Real-time PCR of 13 mature microRNAs differentially expressed in colorectal cancer and non-tumoral tissues", Molecular Cancer, vol. 5, No. 29, (2006), pp. 1-10.
Bartel, D. P. "MicroRNAs: Target Recognition and Regulatory Functions", Cell, vol. 136, (2009), pp. 215-233.
Bhattacharyya, A. et al., "The Breast Cancer Susceptibility Gene *BRCA1* Is Required for Subnuclear Assembly of Rad51 and Survival following Treatment with the DNA Cross-linking Agent Cisplatin", The Journal of Biological Chemistry, vol. 275, No. 31, (2000), pp. 23899-23903.
Boulton, S. J. "Cellular functions of the BRCA tumour-supressor proteins", Biochemistry Society Transactions, vol. 34, Part 5, (2006), pp. 633-645.
Bryant, H. E. et al., "Specific killing of BRCA2-deficient tumours with inhibitors of poly(ADP-ribose) polymerase", Nature, vol. 434, (2005), pp. 913-917.
Calin, G. A. et al., "Chromosomal rearrangements and microRNAs: a new cancer link with clinical implications", The Journal of Clinical Investigation, vol. 117, No. 8, (2007), pp. 2059-2066.
Camps, C. et al., "hsa-mirR-210 is Induced by Hypoxia and is an Independent Prognostic Factor in Breast Cancer", Clin. Cancer Res., vol. 14, No. 5, (2008), pp. 1340-1348.
Catteau, A. et al., "Methylation of the *BRCA1* promoter region in sporadic breast and ovarian cancer: correlation with disease characteristics", Oncogene, vol. 18, (1999), pp. 1957-1965.
Chang, T. C. et al., "MicroRNAs in Vertebrate Physiology and Human Disease", Annu. Rev. Genomics Hum. Genet., vol. 8, (2007), pp. 215-239.
Choudhury, A. et al., "Targeting homologous recombination using imatinib results in enhanced tumor cell chemosensitivity and radiosensitivity", Mol. Cancer Ther., vol. 8, No. 1, (2009), pp. 203-213.
Chowdhury, D. et al., "A PP4-phosphatase Complex Dephosphorylates γ-H2AX Generated During DNA Replication", Molecular Cell, vol. 31, (2008), pp. 33-46.
Croce, C. M. "MicroRNAs and lymphomas", Annals of Oncology, vol. 19, Suppl. 4, (2008), pp. iv39-iv40.
Crosby, M. E. et al., "MicroRNA Regulation of DNA Repair Gene Expression in Hypoxic Stress", Cancer Res., vol. 69, No. 3, (2009), pp. 1221-1229.
Cunliffe, H. E. et al., "The Gene Expression Response of Breast Cancer to Growth Regulators: Patterns and Correlation with Tumor Expression Profiles", Cancer Research, vol. 63, (2003), pp. 7158-7166.

(Continued)

*Primary Examiner* — Jennifer McDonald
(74) *Attorney, Agent, or Firm* — Fish & Richardson P.C.

(57) ABSTRACT

The present disclosure provides methods of determining the levels of BRCA1 in a cell, altering the levels of BRCA1 in a cell, determining the likelihood of developing cancer, and determining the prognosis of a patient with cancer using miR-182 and analogs thereof. Importantly, the invention also provides methods of determining whether a patient should be treated with PARP inhibitors, improving PARP therapy in cancer, as well as methods for selecting and improving genotoxic therapies. Also featured are methods of treating patients with cancers based on the expression levels of miR-182. The invention also features compositions comprising miR-182 and analogs thereof, antagomirs of miR-182 and analogs thereof, in combination with PARP inhibitors and genotoxic agents.

22 Claims, 16 Drawing Sheets

(56) References Cited

OTHER PUBLICATIONS

Douglas-Jones, A. G. et al., "Comparison of core oestrogen receptor (ER) assay with excised tumour: intratumoral distribution of ER in breast carcinoma", J. Clin. Pathol., vol. 54, (2001), pp. 951-955.

Easow, G. et al., "Isolation of microRNA targets by miRNP immunopurification", RNA, vol. 13, (2007), pp. 1198-1204.

Elstrodt, F. et al., "BRCA1 Mutation Analysis of 41 Human Breast Cancer Cell Lines Reveals Three New Deleterious Mutants", Cancer Res., vol. 66, No. 1, (2006), pp. 41-45.

Esteller, M. et al., "Promoter Hypermethylation and BRCA1 Inactivation in Sporadic Breast and Ovarian Tumors", Journal of the National Cancer Institute, vol. 92, No. 7, (2000), pp. 564-569.

Farmer, H. et al., "Targeting the DNA repair defect in BRCA mutant cells as a therapeutic strategy", Nature, vol. 434, (2005), pp. 917-921.

Fedier, A. et al., "The effect of loss of Brca1 on the sensitivity to anticancer agents in p53-deficient cells", International Journal of Oncology, vol. 22, (2003), pp. 1169-1173.

Filipowicz, W. et al., "Mechanisms of post-transcriptional regulation by microRNAs: are the answers in sight?", Nature Review Genetics, vol. 9, (2008), pp. 102-114.

Fong, P. C. et al, "Inhibition of Poly(ADP-Ribose) Polymerase in Tumors from BRCA Mutation Carriers", The New England Journal of Medicine, vol. 361, No. 2, (2009), pp. 123-134.

Foulkes, W. D. et al, "Estrogen Receptor Status in *BRCA1*- and *BRCA2*-Related Breast Cancer: The Influence of Age, Grade, and Histological Type", Clinical Cancer Research, vol. 10, (2004), pp. 2029-2034.

Friedman, L. M. et al., "MicroRNAs are essential for development and function of inner ear hair cells in vertebrate", Proc. Natl. Acad. Sci. USA, vol. 106, No. 19, (2009), pp. 7915-7920.

Gaur, A. et al., "Characterization of MicroRNA Expression Levels and Their Biological Correlates in Human Cancer Cell Lines", Cancer Res., vol. 67, No. 6, (2007), pp. 2456-2468.

Gee, H. E. et al., "MicroRNA-10b and breast cancer metastasis", Nature, vol. 455 (2008), pp. E8-9.

Hanke, M. et al., "A robust methodology to study urine microRNA as Tumor marker: microRNA-126 and microRNA-182 are related to urinary bladder cancer", Urologic Oncology: Seminars and Original Investigations, vol. 28, (2010), pp. 655-661.

Helleday, T. et al., "DNA repair pathways as targets for cancer therapy", Nature Reviews Cancer, vol. 8, (2008), pp. 193-204.

Hendrickson, D. G. et al., "Systematic Identification of mRNAs Recruited to Argonaute 2 by Specific microRNAs and Corresponding Changes in Transcript Abundance", PLoS ONE, vol. 3, Issue 5, (2008), pp. e2126.

Herman, J. G. et al., "Promoter-Region Hypermethylation and Gene Silencing in Human Cancer", Curr Top Microbiol. Immunol., vol. 249, (2000), pp. 35-54.

Hudis, C. A. et al., "Proposal for Standardized Definitions for Efficacy End Points in Adjuvant Breast Cancer Trials: The STEEP System", Journal of Clinical Oncology, vol. 25, No. 15, (2007), pp. 2127-2132.

Jin, Z. B. et al., "Targeted deletion of miR-182, an abundant retinal microRNA", Molecular Vision, vol. 15, (2009), pp. 523-533.

Kennedy, R. D. et al., "The Role of BRCA1 in the Cellular Response to Chemotherapy", Journal of the National Cancer Institute, vol. 96, No. 22, (2004), pp. 1659-1668.

Kertesz, M. et al., "The role of site accessibility in microRNA target recognition", Nature Genetics, vol. 39, No. 10, (2007), pp. 1278-1284.

Kim, H. H. et al., "HuR recruits let-7/RISC to repress c-Myc expression", Genes & Development, vol. 23, (2009), pp. 1743-1748.

Kim, H. et al., "New players in the BRCA1-mediated DNA Damage Responsive Pathway", Molecules and Cells, vol. 25, No. 4, (2008), pp. 457-461.

Lal, A. et al., "miR-24-mediated downregulation of H2AX suppresses DNA repair in terminally differentiated blood cells", Nature Structural & Molecular Biology, vol. 16, No. 5, (2009), pp. 492-498.

Lewis, M. A. et al., "An ENU-induced mutation of miR-96 associated with progressive hearing loss in mice", Nature Genetics, vol. 41, No. 5, (2009), pp. 614-618.

Lord, C. J. et al., "Targeted therapy for cancer using PARP inhibitors", Current Opinion in Pharmacology, vol. 8, (2008), pp. 363-369.

Matros, E. et al., "BRCA1 promoter methylation in sporadic breast tumors: relationship to gene expression profiles", Breast Cancer Research and Treatment, vol. 91, (2005), pp. 179-186.

Mencia, A. et al., "Mutations in the seed region of human miR-96 are responsible for nonsyndromic progressive hearing loss", Nature Genetics, vol. 41, No. 5, (2009), pp. 609-613.

Miranda, K. C. et al., "A Pattern-Based Method for the Identification of MicroRNA Binding Sites and Their Corresponding Heteroduplexes", Cell, vol. 126, (2006), pp. 1203-1217.

Moynahan, M. E. et al., "Brca1 Controls Homology-Directed DNA Repair", Molecular Cell, vol. 4, (1999), pp. 511-518.

Moynahan, M. E. et al., "Homology-directed DNA Repair, Mitomycin-C Resistance, and Chromosome Stability is Restored with Correction of a *Brca1* Mutation", Cancer Research, vol. 61, (2001), pp. 4842-4850.

Mueller, C. R. et al., "Regulation of BRCA1 expression and its relationship to sporadic breast cancer", Breast Cancer Res., vol. 5, (2003), pp. 45-52.

Mullan, P. B. et al., "BRCA1 and GADD45 mediated G2/M cell cycle arrest in response to antimicrotubule agents", Oncogene, vol. 20, (2001), pp. 6123-6131.

Mullan, P. B. et al., "BRCA1—A good predictive marker of drug sensitivity in breast cancer treatment?", Biochima et Biophysica Acta, vol. 1766, (2006), pp. 205-216.

Nakanishi, K. et al., "Human Fanconi anemia monoubiquitination pathway promotes homologous DNA repair", Proc. Natl. Acad. Sci. USA, vol. 102, No. 4, (2005), pp. 1110-1115.

Narod, S. A. et al., "BRCA1 and BRCA2: 1994 and Beyond", Nature Reviews Cancer, vol. 4, (2004), pp. 665-676.

Neve, R. M. et al., "A collection of breast cancer cell lines for the study of functionally distinct cancer subtypes", Cancer Cell, vol. 10, (2006), pp. 515-527.

Palacios, J. et al., "The Molecular Pathology of Hereditary Breast Cancer", Pathobiology, vol. 75, (2008), pp. 85-94.

Perou, C. M. et al., "Molecular portraits of human breast tumors", Nature, vol. 406, (2000), pp. 747-752.

Pierce, M. L. et al., "MicroRNA-183 family conservation and ciliated neurosensory organ expression", Evolution & Development, vol. 10, No. 1, (2008), pp. 106-113.

Ragoussis, J. I., "Combined miRNA/mRNA Signatures in Breast Cancer: Prognostic and Functional Implications", BIT's 3rd World Cancer Congress: Breast Cancer Conference 2010, Theme: Fighting Breast Cancer at Molecular Level, Apr. 25-27, 2010, Abstract, 1 page.

Ratnam, K. et al., "Current Development of Clinical Inhibitors of Poly (ADP-Ribose) Polymerase in Oncology)", Clin Cancer Res, vol. 13, No. 5, (2007), pp. 1383-1388.

Rice, J. C. et al., "Methylation of the BRCA1 promoter is associated with decreased BRCA1 mRNA levels in clinical breast cancer specimens", Carcinogenesis, vol. 21, No. 9, (2000), pp. 1761-1765.

San Filippo, J. et al., "Mechanism of Eukaryotic Homologous Recombination", Ann. Rev. Biochem., vol. 77, (2008), pp. 229-257.

Scully, R. et al., "Genetic Analysis of BRCA1 Function in a Defined Tumor Cell Line", Molecular Cell, vol. 4, (1999), pp. 1093-1099.

Segura, M. F. et al., "Aberrant miR-182 expression promotes melanoma metastasis by repressing FOXO3 and microphthalmia-associated transcription factor", Proc. Natl. Acad. Sci. USA, vol. 106, No. 6, (2009), pp. 1814-1819.

Sethupathy, P. et al., "A guide through present computational approaches for the identification of mammalian microRNA targets", Nature Methods, vol. 3, No. 11, (2006), pp. 881-886.

Shen, J. et al., "Novel genetic variants in microRNA genes and familial breast cancer", Int. J. Cancer, vol. 124, (2009), pp. 1178-1182.

Shkumatava, A. et al., "Coherent but overlapping expression of microRNAs and their targets during vertebrate development", Genes & Development, vol. 23, (2009), pp. 466-481.

(56) References Cited

OTHER PUBLICATIONS

Tan, L. P. et al., "A high throughput experimental approach to identify miRNA targets in human cells", Nucleic Acids Research, vol. 37, No. 20, (2009), pp. e137.

Thompson, M. E. et al., "Decreased expression of BRCA1 accelerates growth and is often present during sporadic breast cancer progression", Nature Genetics, vol. 9, (1995), pp. 444-450.

Turner, N. C. et al., "BRCA1 dysfunction in sporadic basal-like breast cancer", Oncogene, vol. 26, (2007), pp. 2126-2132.

Turner, N. et al., "Hallmarks of 'BRCAness' in sporadic cancers", Nature Reviews Cancer, vol. 4, (2004), pp. 814-819.

Van Den Eynden, G. G. et al., "Validation of a tissue microaaray to study differential protein expression in inflammatory and non-inflammatory breast cancer", Breast Cancer Research and Treatment, vol. 85, (2004), pp. 13-22.

Ventura, A. et al., "MicroRNAs and Cancer: Short RNAs Go a Long Way", Cell, vol. 136, (2009), pp. 586-591.

Wilson, C. A. et al., Localization of human BRCA1 and its loss in high-grade, non-inherited breast carcinomas, Nature Genetics, vol. 21, (1999), pp. 236-240.

Xu, B. et al., "Involvement of BRCA1in S-phase and $G_2$-phase Checkpoints after Ionizing Irradiation", Molecular and Cellular Biology, vol. 21, No. 10, (2001), pp. 3445-3450.

Xu, S. et al., "MicroRNA (miRNA) Transcriptome of Mouse Retina and Identification of a Sensory Organ-Specific miRNA Cluster", Journal of Biological Chemistry, vol. 282, No. 34, (2007), pp. 25053-25066.

Yarden, R. I. et al., "BRCA1 regulates the G2/M checkpoint by activating Chk1 kinase upon DNA damage", Nature Genetics, vol. 30, (2002), pp. 285-289.

Zhang, L. et al., "MicroRNAs exhibit high frequency genomic alterations in human cancer", Proc. Natl. Acad. Sci. USA, vol. 103, No. 24, (2006), pp. 9136-9141.

* cited by examiner

MIR-182 IN THE DIAGNOSIS AND TREATMENT OF CANCER

CROSS REFERENCE TO RELATED APPLICATION

This application claims priority to U.S. Provisional Application No. 61/294,946, filed on Jan. 14, 2010, the disclosure of which is incorporated by reference in its entirety in this application.

TECHNICAL FIELD

This invention relates to the regulation of gene expression using microRNAs, and more particularly to, methods of diagnosing cancer, selecting suitable cancer therapies, and cancer prognosis based on microRNA expression levels, as well as methods of treating cancers using microRNAs and antagomirs.

BACKGROUND

BRCA1 is a tumor suppressor gene that is a key factor in responding to DNA damage. Mutations or deregulated expression of breast cancer susceptibility gene 1 (BRCA1) are associated with a significant increase in breast cancer as well as ovarian, cervical, uterine, pancreatic, colon, testicular and prostate cancers as well as melanomas.

Even with improved diagnostic techniques and treatment, cancer remains one of the leading causes of death. Excluding cancers of the skin, breast cancer is the most common cancer diagnosed among U.S. women, accounting for more than 25% of the cancers. Breast cancer is the second leading cause of cancer death in women, after lung cancer. The American Cancer Society (ACS) estimates that in 2009 an estimated 192,370 new cases of invasive breast cancer will be diagnosed among women and 1,910 new cases among men. The ACS also estimates that 40,170 women and 440 men are expected to die from breast cancer.

Between 5-10% of breast cancer patients have an inherited mutation(s) in BRCA1. The remaining 90-95% of breast cancer patients have the sporadic form of the disease. Although decreased expression of BRCA1 is a good indicator of breast cancer and its prognosis, a major difficulty is accurately measuring the levels of BRCA1 in cells. In addition, the levels of BRCA1 can assist a health care provider in determining the type of therapy to be utilized to assist a patient. Accordingly, improved methods of determining the levels of BRCA1 in a cell are urgently needed.

SUMMARY

This invention is based, at least in part, on the discovery that microRNA 182 (miR-182) downregulates BRCA1. This downregulation is mediated through the binding of miR-182 to one or more of at least four miR-182 binding sites in the 3' untranslated region (UTR) of BRCA1 mRNA. miR-182 expression inversely correlates with BRCA1 protein levels in estrogen receptor (ER) negative breast tumor lines as well as in ER-negative primary breast tumor tissue. There is a statistically significant inverse correlation of miR-182 expression with survival of patients with ER-negative breast tumors expressing high levels of BRCA1 mRNA. Antagonizing miR-182 enhances BRCA1 protein levels and protects cells from ionizing radiation (IR) or poly (ADP-ribose) polymerase (PARP) inhibitor-induced cell death, whereas overexpressing miR-182 reduces BRCA1 protein levels, impairs homologous recombination-mediated DNA double strand break (DSB) repair, and renders cells hypersensitive to PARP inhibitors. These results indicate that miR-182-mediated regulation of BRCA1 impacts both tumorigenesis and clinical outcome.

In one aspect, the disclosure features a method of determining the level of BRCA1 in a cell by measuring a level of miR-182 in the cell. The cell is determined to have a lower level of BRCA1 compared to a control cell if the level of miR-182 in the cell is higher than the level of miR-182 in the control cell. The cell can be a cell that is suspected of being a cancer cell, a cell from a tissue suspected of being a cancerous tissue, or a cancer cell. The cancer cell includes, but is not limited to a breast cancer cell, an ovarian cancer cell, a prostate cancer cell, a bladder cancer cell, a testicular cancer cell, a cervical cancer cell, a uterine cancer cell, a pancreatic cancer cell, a colon cancer cell, a leukemia cell, a lymphoma cell, and a melanoma. In a specific embodiment, the cancer cell is a sporadic breast cancer cell that is estrogen receptor (ER)-negative. The level of miR-182 in the cell can be measured by any method known in the art including quantitative polymerase chain reaction (qPCR).

In another aspect, the disclosure features a method of determining the likelihood that an individual will develop cancer. The method includes the steps of: providing a cell from the individual; measuring a level of miR-182 in the cell; and comparing the level of miR-182 in the cell of the individual to a control cell. The individual is determined to have a higher likelihood of developing cancer if the level of miR-182 in the cell from the individual is higher than the level of miR-182 in a control cell from a corresponding tissue obtained from an individual without cancer. The individual is not determined to have a higher likelihood of developing cancer if the level of miR-182 in the cell from the individual is not higher than the level of miR-182 in a control cell from a corresponding tissue obtained from an individual without cancer. The cancer includes, but is not limited to: a breast cancer, an ovarian cancer, a prostate cancer, a bladder cancer cell, a testicular cancer, a cervical cancer, a uterine cancer, a pancreatic cancer, a colon cancer, a leukemia, a lymphoma, and a melanoma. In a specific embodiment, the cancer is ER-negative sporadic breast cancer. For each of these cancers, the control cell can be the corresponding normal epithelial cell. Thus, in one embodiment of this aspect, the cell is a breast epithelial cell, the control cell is a normal breast epithelial cell, and the cancer is breast cancer. In another embodiment of this aspect, the cell is an ovarian cell, the control cell is a normal ovarian epithelial cell, and the cancer is ovarian cancer. The level of miR-182 in the cell can be measured by qPCR.

In yet another aspect, the disclosure features a method of determining the prognosis of a patient having a cancer expressing high or comparable levels of BRCA1 mRNA relative to a corresponding non-cancerous cell. The method includes the steps of: providing a sample from the patient; and measuring a level of miR-182 in at least one cell of the sample. The patient is determined to have a poor prognosis if the level of miR-182 in the sample is higher than the level of miR-182 in a corresponding control sample obtained from an individual without cancer. The patient is determined to have a good prognosis if the level of miR-182 in the sample is the same or lower than the level of miR-182 in a corresponding control sample obtained from an individual without cancer. The cancer expressing high or comparable levels of BRCA1 mRNA can be, but is not limited to, breast cancer, ovarian cancer, prostate cancer, bladder cancer, testicular cancer, cervical cancer, uterine cancer, pancreatic cancer, skin cancer, colon cancer, leukemia, lymphoma, and melanoma. In one embodiment of this aspect, the patient has breast cancer. In a preferred embodiment, the patient has ER-negative sporadic breast cancer. In another embodiment, the patient has ovarian cancer. The level of miR-182 in the cell can be measured by qPCR. The sample from the patient may be a biopsy sample or a blood sample.

In another aspect, the disclosure provides a method of determining whether to treat a patient with a PARP inhibitor. The method includes: providing a sample from the patient and measuring a level of miR-182 in the sample. The patient is identified as a suitable candidate for treatment with a PARP inhibitor if the level of miR-182 in the sample is higher than a level of miR-182 in a control sample. In contrast, the patient is not identified as being suitable for treatment with a PARP inhibitor if the level of miR-182 in the sample is lower than a level of miR-182 in a control sample. The patient may have breast cancer, ovarian cancer, prostate cancer, testicular cancer, cervical cancer, uterine cancer, pancreatic cancer, colon cancer, skin cancer, leukemia, or a lymphoma. In one embodiment of this aspect, the patient has breast cancer. In a preferred embodiment, the patient has ER-negative sporadic breast cancer. In another embodiment, the patient has ovarian cancer. The level of miR-182 in the cell can be measured by qPCR. The sample from the patient may be a biopsy sample from a cancerous tissue or a tissue suspected of being cancerous. In certain embodiments, the biopsy sample is from a cancerous breast of the patient or a breast suspected of being cancerous. In other embodiments, the biopsy sample is from a cancerous ovary of the patient or an ovary suspected of being cancerous. The sample can also be a blood sample. The control sample used in the methods of this aspect can be a sample obtained from a corresponding tissue of an individual without cancer. In the case of solid tissues, the control sample is a normal epithelial cell from the tissue corresponding to the tissue with cancer.

In another aspect, the disclosure describes a method of decreasing the level of BRCA1 in a cell of a subject in need thereof. The method comprises introducing miR-182 or an analog thereof into the cell. The cell can be one of: a breast cell, an ovarian cell, a prostate cell, a bladder cancer cell, a testicular cell, a cervical cell, a uterine cell, a pancreatic cell, a colon cell, and a skin cell. The cell may be a cancer cell, or suspected of being a cancer cell. The cancer cell may be a breast cancer cell, an ovarian cancer cell, a prostate cancer cell, a testicular cancer cell, a cervical cancer cell, a uterine cancer cell, a pancreatic cancer cell, colon cancer cell, a melanoma cell, a leukemia cell, or a lymphoma cell. In a preferred embodiment, the cell is an ER-negative sporadic breast cancer cell. The method of this aspect can further include a step of measuring the level of BRCA1 protein in the cell or any gene known to be regulated by BRCA1. The subject can be a human. The method can also be practiced ex vivo. In some embodiments of this aspect, prior to introducing miR-182 or an analog thereof into the cell, a sample from the subject is determined to have a higher level of BRCA1 than a control cell.

In another aspect, the disclosure provides a method of increasing the level of BRCA1 in a cell of a subject in need thereof. The method comprises introducing an antagomir of miR-182 or an analog thereof into the cell. The cell can be one of: a breast cell, an ovarian cell, a prostate cell, a bladder cancer cell, a testicular cell, a cervical cell, a uterine cell, a pancreatic cell, a colon cell, and a skin cell. The cell may be a cancer cell, or suspected of being a cancer cell. The cancer cell may be a breast cancer cell, an ovarian cancer cell, a prostate cancer cell, a testicular cancer cell, a cervical cancer cell, a uterine cancer cell, a pancreatic cancer cell, colon cancer cell, a melanoma cell, a leukemia cell, or a lymphoma cell. The method of this aspect can further include a step of measuring the level of BRCA1 protein in the cell or any gene known to be regulated by BRCA1. The subject can be a human. The method can also be practiced ex vivo. In some embodiments of this aspect, prior to introducing miR-182 or an analog thereof into the cell, a sample from the subject is determined to have a lower level of BRCA1 than a control cell.

In another aspect, the disclosure provides a method of treating a patient having or suspected of having a cancer. The method involves providing a patient identified as having cells that express higher levels of miR-182 compared to a normal epithelial cell from a corresponding tissue of an individual without cancer, and administering to the patient a PARP inhibitor. The cancer includes, but is not limited to, a breast cancer, ovarian cancer, prostate cancer, testicular cancer, cervical cancer, uterine cancer, pancreatic cancer, colon cancer, skin cancer, leukemia, lymphoma, and melanoma. In a preferred embodiment, the patient has ER-negative sporadic breast cancer. The PARP inhibitor includes, but is not limited to, 4-Amino-1,8-naphthalimide (ANI), ABT-888 (Abbot Labs), KU59436 (AstraZeneca), AZD2281/Olaparib (Astra-Zeneca), AG014699 (Pfizer), BSI-201 (BiPar), INO-1001 (Genentech), and GPI 21016 (MGI Pharma). In one embodiment, the method may further involve administering miR-182 or an analog thereof to the patient. In another embodiment, the method further includes administering radiotherapy and/or chemotherapy to the patient. The miR-182 or analog thereof, or radiotherapy and/or chemotherapy can be administered at substantially the same time as, prior to, or subsequent to administration of the PARP inhibitor.

In yet another aspect, the disclosure provides a method of treating sporadic breast cancer in a patient. The method includes administering to the patient an amount of miR-182 effective to lower BRCA1 levels in the cancer cells of the patient and a PARP inhibitor. The PARP inhibitor can be, but is not limited to, 4-Amino-1,8-naphthalimide (ANI), ABT-888 (Abbot Labs), KU59436 (AstraZeneca), AZD2281/Olaparib (Astra-Zeneca), AG014699 (Pfizer), BSI-201 (BiPar), INO-1001 (Genentech), or GPI 21016 (MGI Pharma). The miR-182 and the PARP inhibitor can be administered sequentially or at substantially the same time. The method may further include administering radiotherapy and/or chemotherapy to the patient.

In another aspect, the disclosure features a method for improving PARP therapy in a patient. The method involves administering to the patient an amount of miR-182 effective to lower the BRCA1 levels in a cell to be targeted by the PARP therapy prior to, at substantially the same time as, or after administration of a PARP inhibitor. In some embodiments, the patient has cancer. The cancer can be breast cancer, ovarian cancer, prostate cancer, testicular cancer, cervical cancer, uterine cancer, pancreatic cancer, colon cancer, and melanoma. In specific embodiments, the patient has ovarian cancer or ER-negative sporadic breast cancer. In some embodiments, the patient is suspected of having cancer or is a pre-cancerous. The PARP inhibitor can be, but is not limited to: 4-Amino-1,8-naphthalimide (ANI), ABT-888 (Abbot Labs), KU59436 (AstraZeneca), AZD2281/Olaparib (Astra-Zeneca), AG014699 (Pfizer), BSI-201 (BiPar), INO-1001 (Genentech), or GPI 21016 (MGI Pharma).

In another aspect, the disclosure features a method of determining treatment of a patient with cancer. The method involves: providing a sample from the patient and determining a level of miR-182 in one or more cells in the sample. If the level of miR-182 is determined to be higher than a level of miR-182 in a control sample, the patient is identified as a suitable candidate for treatment with a first agent that can be effective against cancers expressing a low level of BRCA1. If the level of miR-182 is determined to be lower than a level of miR-182 in a control sample, the patient is identified as a suitable candidate for treatment with a second agent that can be effective against cancers expressing a high level of BRCA1. The first agent includes, but is not limited to: an alkylating agent, a topoisomerase inhibitor, an antimetabolite, an anthracycline, an antitumor antibiotic, and an epipodophyllotoxin. The second agent includes, but is not limited to a spindle toxin such as taxanes and vinca alkaloids. In specific embodiments, the spindle toxin can be: paclitaxel, vincristine, vinblastine, vinorelbine, or vindesine.

In another aspect, the disclosure provides a method for improving the response of a patient to a genotoxic agent. The method involves administering to the patient an amount of miR-182 effective to lower the level of BRCA1 in the cells being targeted by the genotoxic agent prior to, substantially at the same time as, or after administration of the genotoxic agent. The genotoxic agent can be a chemotherapeutic agent such as carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gencitabine, cisplatin (CDDP), adriamycin (ADR), or any analogs thereof. The genotoxic agent can be an ionizing radiation such as gamma-radiation, X-irradiation, infrared, UV-radiation, and beta-radiation.

In yet another aspect, the disclosure features a kit containing a PARP inhibitor and miR-182 or an analog thereof. The PARP inhibitor includes, but is not limited to, 4-Amino-1,8-naphthalimide (ANI), ABT-888 (Abbot Labs), KU59436 (AstraZeneca), AZD2281/Olaparib (Astra-Zeneca), AG014699 (Pfizer), BSI-201 (BiPar), INO-1001 (Genentech), and GPI 21016 (MGI Pharma).

In another aspect, the disclosure features a kit that includes a genotoxic agent and miR-182. The genotoxic agent can be a chemotherapeutic agent, e.g., carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gencitabine, cisplatin (CDDP), adriamycin (ADR), or any analog thereof.

In a further aspect, the disclosure provides a spindle poison and a miR-182 antagomir or an analog thereof. The spindle poison can be a taxane or a vinca alkaloid. In specific embodiments, the spindle toxin can be paclitaxel, vincristine, vinblastine, vinorelbine, or vindesine.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can also be used in the practice or testing of the present invention. All publications, patent applications, patents, and other references mentioned herein are incorporated by reference in their entirety. The materials, methods, and examples disclosed herein are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 2:
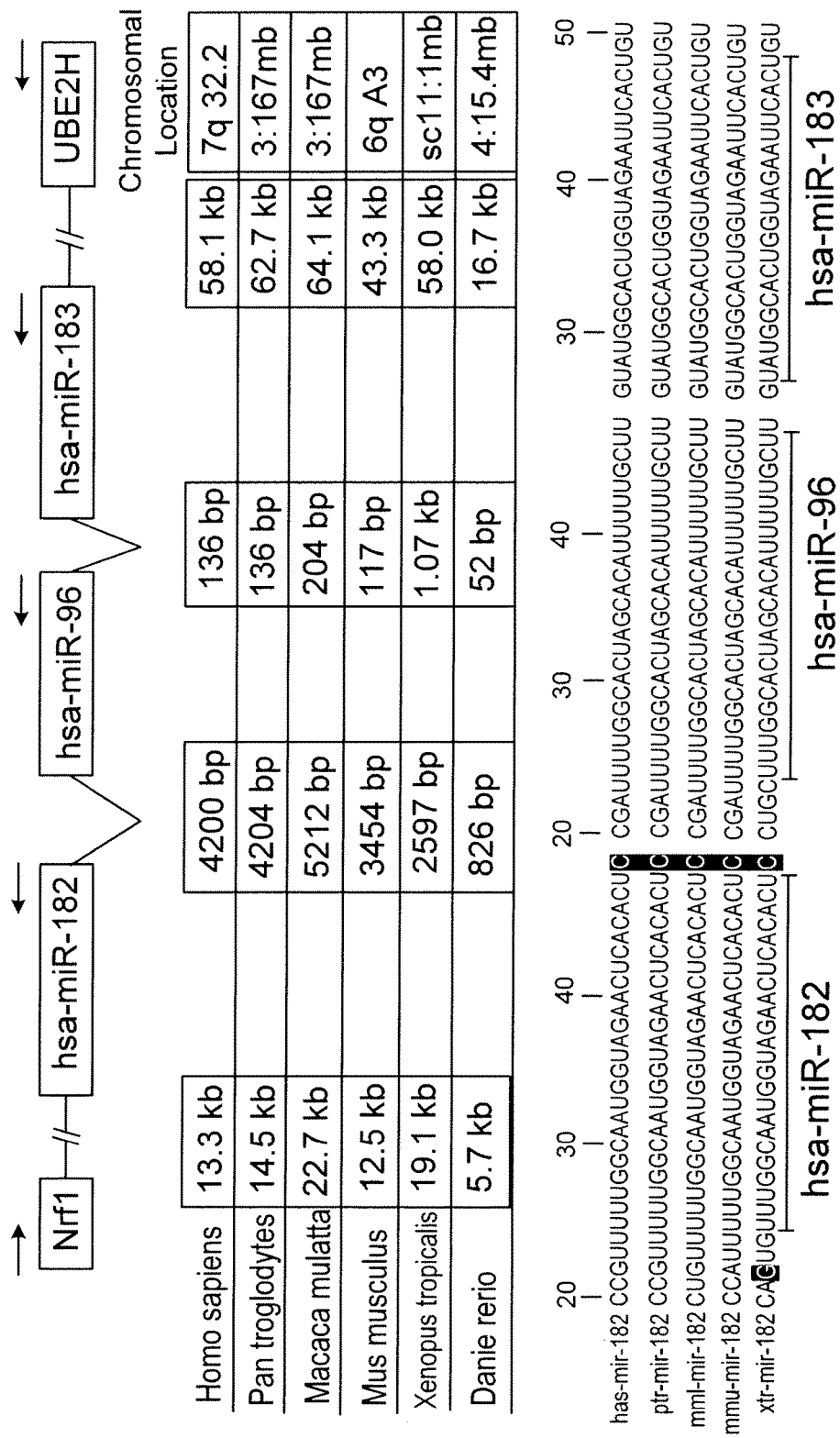
FIG. 2 is a schematic representation of the chromosomal location of the miR-183 cluster and a sequence alignment of miR-183 cluster in different species including *Homo sapiens* (hsa-miR-182 (SEQ ID NO: 29); hsa-miR-96 (SEQ ID NO:30); hsa-miR-183 (SEQ ID NO:31)); *Pan troglodytes* (ptr-mir-182 (SEQ ID NO:32); ptr-miR-96 (SEQ ID NO:33); ptr-mir-183 (SEQ ID NO:34)); *Macaca mulatta* (mml-mir-182 (SEQ ID NO:35); mml-miR-96 (SEQ ID NO:36); mml-mir-183 (SEQ ID NO:37)); *Mus musculus* (mmu-mir-182 (SEQ ID NO:38); mmu-miR-96 (SEQ ID NO:39); mmu-mir-183 (SEQ ID NO:40)); and *Xenopus tropicalis* xtr-mir-182 (SEQ ID NO:41); xtr-miR-96 (SEQ ID NO:42); xtr-mir-183 (SEQ ID NO:43)).

The BRCA1 gene encodes a 220-kDa nuclear protein that responds to DNA damage by participating in cellular pathways responsible for DNA repair. Loss-of-function mutations in BRCA1 are associated with a high risk of developing cancer. It has been reported that an individual with a loss-of-function mutation in BRCA1 has up to an 82% risk of developing breast cancer and up to a 54% risk of developing ovarian cancer by age 80. In addition to cancers of the breast and ovary, inappropriate expression or deregulation of BRCA1 is also associated with cancers of other organs, including, the stomach, pancreas, prostate, colon, and skin (e.g., melanoma). BRCA1 deregulation is also associated with leukemias and lymphomas, including mantle cell lymphoma, acute myeloid leukemia, acute lymphocytic leukemia, chronic lymphocytic leukemia, and prolymphocytic leukemia. Germline mutations in BRCA1 account for only about 5-10% of cancer cases. In 90-95% of cancers, lower than normal expression of BRCA1 is an important contributing factor. The invention, relates in part, to the finding that BRCA1 mRNA levels are downregulated by microRNA-182 (miR-182). The identification of miR-182-mediated regulation of BRCA1 has important implications in diagnosis, prognosis, and treatment of BRCA1-associated cancers. Various aspects of the invention are described below.

miR-182 and Antagomirs of miR-182 microRNAs (miRNAs) are single-stranded RNA molecules of about 21-24 nucleotides in length that regulate gene expression. miRNAs are transcribed from DNA, but the miRNAs are not translated into protein (i.e., they are non-coding RNAs). Instead, each primary transcript (a pri-miRNA) is processed into a short stem-loop structure called a pre-miRNA and finally into a linear functional miRNA (generally a 22 base pair piece of RNA). Mature miRNA molecules are either fully or partially complementary to regions (typically in the 3'-UTR, surrounding the stop codon, or within the 5'-UTR) of one or more messenger RNA (mRNA) molecules. They regulate post-transcriptional gene expression by blocking translation of target mRNAs, reducing stability of the target mRNA, or by accelerating their degradation. Generally, if an mi-RNA is fully complementary to a target region of an mRNA, the mi-RNA accelerates the targeted degradation of the mRNA. If, however, an mi-RNA is partially complementary to a target region of an mRNA, the mi-RNA simply blocks the translation of the mRNA. To date, more than 700 human miRNAs have been identified, regulating an estimated 30% of all human genes. miRNAs important roles in several biological processes such as cell proliferation, apoptosis, developmental timing, and DNA repair.

miRNA cluster-183 consists of three miRNAs namely, miR-96, miR-183 and miR-182 (FIG. 2). These miRNAs are encoded in a 5-kb gene segment and are processed from the same polycistronic transcript on human chromosome 7q32.2 with conservation of synteny on mouse chromosome 6qA3. These miRNAs are expressed at high levels in mouse retina and sensory hair cells of the ear and are thought to have a sensory role.

miR-182 has the sequence 5' UUU GGC AAU GGU AGA ACU CAC ACU 3' (SEQ ID NO:1). The 9 base pair sequence 5' UUU GGC AAU 3' (SEQ ID NO:2) is called the "seed region" and is the sequence within miR-182 that is primarily involved in binding the target sequence in the mRNA. The folding and thermodynamic energy of the 15 base pair sequence 5' GGU AGA ACU CAC ACU 3' (SEQ ID NO:3) that is 3' to the seed region contributes to target recognition and binding by the seed sequence.

Like many other miRNAs, miR-182 can bind to partially complementary sites in its target mRNA. miR-182 has four binding sites in the 3'UTR of BRCA1. The sequence of the 3'UTR of BRCA1 is provided below and the four miR-182 binding sites (the target sites) at positions 888-902, 908-932, 941-965 and 955-979 in the 3'UTR are boldened and underlined:

(SEQ ID NO: 4)
5' CTGCAGCCAGCCACAGGTACAGAGCCACAGGACCCCAAGAATGAGC

TTACAAAGTGGCCTTTCCAGGCCCTGGGAGCTCCTCTCACTCTTCAGTC

CTTCTACTGTCCTGGCTACTAAATATTTTATGTACATCAGCCTGAAAAG

GACTTCTGGCTATGCAAGGGTCCCTTAAAGATTTTCTGCTTGAAGTCTC

CCTTGGAAATCTGCCATGAGCACAAAATTATGGTAATTTTTCACCTGAG

AAGATTTTAAAACCATTTAAACGCCACCAATTGAGCAAGATGCTGATTC

ATTATTTATCAGCCCTATTCTTTCTATTCAGGCTGTTGTTGGCTTAGGG

CTGGAAGCACAGAGTGGCTTGGCCTCAAGAGAATAGCTGGTTTCCCTAA

GTTTACTTCTCTAAAACCCTGTGTTCACAAAGGCAGAGAGTCAGACCCT

TCAATGGAAGGAGAGTGCTTGGGATCGATTATGTGACTTAAAGTCAGAA

TAGTCCTTGGGCAGTTCTCAAATGTTGGAGTGGAACATTGGGGAGGAAA

TTCTGAGGCAGGTATTAGAAATGAAAAGGAAACTTGAAACCTGGGCATG

GTGGCTCACGCCTGTAATCCCAGCACTTTGGGAGGCCAAGGTGGGCAGA

TCACTGGAGGTCAGGAGTTCGAAACCAGCCTGGCCAACATGGTGAAACC

CCATCTCTACTAAAAATACAGAAATTAGCCGGTCATGGTGGTGGACACC

TGTAATCCCAGCTACTCAGGTGGCTAAGGCAGGAGAATCACTTCAGCCC

GGGAGGTGGAGGTTGCAGTGAGCCAAGATCATACCACGGCACTCCAGCC

TGGGTGACAGTGAGACTGTGGCTCAAAAAAAAAAAAAAAAAAGGAAAA

TGAAACTAGAAGAGATTTCTAAAAGTCTGAGATATATTTGCTAGATTTC

TAAAGAATGTGTTCTAAAACAGCAGAAGATTTTCAAGAACCGGTTTCCA

AAGACAGTCTTCTAATTCCTCATTAGTAATAAGTAAAATGTTTATTGTT

GTAGCTCTGGTATATAATCCATTCCTCTTAAAATATAAGACCTCTGGCA

TGAATATTTCATATCTATAAAATGACAGATCCCACCAGGAAGGAAGCTG

GTTGCTTTCTTTGAGGTATTTTTTTCCTTTGCTCCCTGTTGCTGAAACC

ATACAGCTTCATAAATAATTTTGCTTGCTGAAGGAAGAAAAAGTGTTTT

TCATAAACCCATTATCCAGGACTGTTTATAGCTGTTGGAAGGACTAGGT

CTTCCCTAGCCCCCCCAGTGTGCAAGGGCAGTGAAGACTTGATTGTACA

AAATACGTTTTGTAAATGTTGTGCTGTTAACACTGCAAATAAACTTGGT

AGCAAACACTTC 3'

An alignment of the miR-182 sequence with the four binding sites in the 3'UTR of BRCA1 mRNA is provided below. The miR-182 sequence is listed in the 3'→5' direction and the BRCA1 3'UTR sequences are listed in the 5'→3' direction. The underlined region corresponds to the 9 base pair "seed region" of miR-182

(SEQ ID NO: 1)
miR-182: 3' UCA CAC UCA AGA UGG <u>UAA CGG UUU</u> 5'

(SEQ ID NO: 5)
888-902: 5' AUG AAA CUA GAA GAG AUU UCU AAA 3'

-continued (SEQ ID NO: 6)
908-932: 5' AGA UAU AUU UGC UAG AUU UCU AAA 3'

(SEQ ID NO: 7)
941-965: 5' CUA AAA CAG CAG AAG AUU UUC AAG 3'

(SEQ ID NO: 8)
955-979: 5' GAU UUU CAA GAA CCG GUU UCC AAA 3' miR-182 can bind to the four binding sites in the 3'UTR of BRCA1 despite the significant number of mismatches between the region upstream of the seed region of miR-182 and the region upstream of the miR-182 seed region target binding sequence on the BRCA1 mRNA. Thus, the 15 base pair region upstream of the seed region of miR-182 can have 0, 1, 2, 3, 4, 5, 6, 7, 8, 9, 10, 11, 12, 13, 14, or even 15 mismatches with the region upstream of the miR-182 seed region target binding sequence on the BRCA1 mRNA. miR-182 can also bind a target if there are a few mismatches between miR-182 and the target mRNA in the seed region. For example, the 9 base pair seed region of miR-182 can have 0, 1, 2, 3, or 4 mismatches with the target mRNA sequence in the seed region of miR-182. In preferred embodiments, miR-182 only has 0, 1, or 2 mismatches with the target mRNA sequence in the seed region. In certain embodiments, the mismatches in the seed region are in the outermost base pair(s) at the 5' or 3' end of the seed region, or any of the three base pairs of the central three base pairs of the seed region. miR-182 can also be modified to reduce the length of the 24 base pair sequence to between about 16 to about 22 base pairs. In these embodiments, the reduction in length is in the region outside the "seed region" preferably at the 3' end of the sequence. One of ordinary skill can readily make changes in the miR-182 sequence to create miR-182 variants that retain the ability to bind miR-182 binding sites in target mRNAs and retain their ability to interfere with the translation of the mRNAs. In addition, based on the above teachings, one of ordinary skill can make variants of the miR-182 binding sites that still retain the ability to bind miR-182. In certain embodiments, the miR-182 binding sites is 75%, 80%, 85%, 90%, 95%, 96%, 97%, 98%, or 99% identical to any one of SEQ ID NOS: 5, 6, 7, or 8. In determining which nucleotides to vary in the miR-182 binding site, the binding site of the miR-182 9 base pair seed region should either be fully complementary to miR-182 or have at most 4, 3, 2 or 1 mismatch. Significant variability is permitted in the 15 base pair region upstream of the region to which the miR-182 seed region binds. Thus, there can be 1, 2, 3, 4, 5, 6, 7, 8, 9, 10, 11, 12, 13 or 14 mismatches in this region.

The BRCA1 3'UTR miR-182 binding sites or variants thereof can be introduced in a nucleic acid sequence to create nucleic acid sequences that can be regulated by miR-182. One or more miR-182 binding sites can be introduced in the nucleic acid that is to be placed under the control of miR-182. These binding sites may be introduced any where in the nucleic acid but preferably around the stop codon of the nucleic acid and most preferably, within the 3'UTR of the nucleic acid. The binding sites for miR-182 can have 0, 1, 2, 3, 4, 5, 6, 7, 8, 9, 10, 11, 12, 13, 14, or even 15 mismatches with the miR-182 sequence. The binding sites can also bind miR-182 if there are a few mismatches between the binding site and miR-182 in the seed region. For example, the 9 base pair seed region of the binding site can have 0, 1, 2, 3, or 4 mismatches with miR-182. In preferred embodiments, the binding site(s) has only has 0, 1, or 2 mismatches with the miR-182 sequence in the seed region.

In addition, in view of the description herein of the miR-182 binding site and the potential variations in sequences that are permitted within the miR-182 binding site, one of ordinary skill can also readily identify mRNAs that are regulated by miR-182. The easiest way to identify miR-182 targets is to use the seed region and variants thereof and search a mRNA sequence library. If the mRNA is regulated by miR-182, the miR-182 binding site is likely to be in the 3'UTR or in some cases even in the 5'UTR of the mRNA.

The invention also features antagomirs of miR-182 and variants thereof. An antagomir is a small synthetic RNA that is perfectly or almost perfectly complementary to the specific miRNA target. Antagomirs inhibit their microRNA target by irreversibly binding the miRNA. Antagomirs are now used as a method to constitutively inhibit the activity of specific miRNAs. Variants of miR-182 antagomirs include molecules having 0, 1, 2, or 3 mismatches with the miR-182 sequence. Preferably the mismatches are outside the seed region.

The microRNAs and antagomirs of the invention can be optionally chemically modified to introduce or improve a desired property of the molecule. For example, modifications can be made to increase serum stability, half-life, and/or permeability into cells when administered in vivo. Examples of serum stability-enhancing chemical modifications include phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. In addition, a variety of 2' modifications are known in the art. The ordinary artisan can readily make a broad spectrum of chemical modifications to microRNAs of the invention without negatively impacting its properties.

miR-182 can be isolated from a biological sample or chemically synthesized. Methods of synthesizing nucleic acids are well known in the art (e.g., using appropriately protected ribonucleoside phosphoramidites and a conventional DNA/RNA synthesizer). miR-182 and antagomirs of miR-182 can also be produced by recombinant methods. These methods include the use of vectors (viral and non-viral), plasmids, cosmids, and any other vehicle for delivering a nucleic acid to a host cell to produce large quantities of the desired molecule. For example, the microRNAs and antagomirs described herein can be expressed from recombinant circular or linear plasmids using any suitable promoter. Non-limiting examples of promoters for expressing RNA from a plasmid include, the U6 or H1 RNA Pol III promoter sequences or the cytomegalovirus promoters. Selection of other suitable promoters is within the skill in the art. Recombinant vectors can also include inducible or regulatable promoters for expression of the microRNA and/or antagomirs in cancer cells. The expression vectors can also be used in the context of a cell free system so long as the reagents for generating and processing the microRNAs are present.

The microRNAs and antagomirs described herein can also be expressed from recombinant viral vectors. Non-limiting examples of viral vectors that can be used to express the microRNAs and antagomirs of the invention include: adenovirus, adeno-associated virus, retroviruses (e.g., lentiviruses, rhabdoviruses, murine leukemia virus), and herpes virus. The tropism of the viral vectors can be modified by pseudotyping the vectors with envelope proteins or other surface antigens from other viruses, or by substituting different viral capsid proteins, as appropriate. For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art.

It will be understood in methods of the invention that a cell or other biological matter such as an organism (including human patients) can be provided a miRNA or antagomir molecule corresponding to a particular miRNA or antagomir by administering to the cell or organism a nucleic acid molecule that functions as the corresponding miRNA or antagomir once inside the cell. The form of the molecule provided to the cell may not be the form that acts a miRNA or antagomir once inside the cell. Thus, it is contemplated that in some embodiments, a synthetic or a nonsynthetic miRNA is provided such that it becomes processed into a mature and active miRNA/antagomir once it has access to the cell's miRNA processing machinery. In certain embodiments, it is specifically contemplated that the miRNA molecule provided is not a mature miRNA molecule but a nucleic acid molecule that can be processed into the mature miRNA once it is accessible to miRNA processing machinery.

Diagnostic Assays

The invention features diagnostic assays. Such assays are based on the finding that BRCA1 is down-regulated by miR-182. As BRCA1 levels are an important indicator of the risk of developing a cancer or whether one in fact has an undetected cancer, assays that determine or assess the levels or relative levels (compared with normal (i.e., non-cancerous) cells) of BRCA1 can serve important therapeutic and prognostic purposes.

Directly determining the level of BRCA1 protein in a tissue is often problematic. A major problem is that the BRCA1 mRNA is not an accurate indicator of BRCA1 protein. Accurately quantifying the amount of any protein in a tissue is a challenge and the rate-limiting step for detection is the quality of the antibody used. The available BRCA1 antibodies can only be used for detection but not accurate estimation of BRCA1 protein in tissue. Another problem with BRCA1 detection is that the amount of tissue required for BRCA1 staining by immunohistochemistry (IHC) is a lot more than is readily available. This invention solves this problem by measuring miR-182, a molecule that regulates BRCA1 at the level of translation, that is readily quantifiable. miR-182 binds to one or more of the four microRNA target binding sites in the 3'-untranslated region (3'-UTR) of BRCA1 and inhibits the translation of the BRCA1 mRNA. In addition, the amount of tissue needed for measuring microRNA levels is significantly less than that needed for IHC.

The diagnostic assays of the invention are generally directed to: (1) determining or assessing the levels or relative levels of BRCA1 in a cell; (2) determining the likelihood that an individual will develop cancer; and (3) determining the prognosis of a patient having a cancer expressing high or comparable levels of BRCA1 mRNA relative to a noncancerous cell. All of these assays generally involve determining or assessing the levels or relative levels of BRCA1 by measuring the level of miR-182 in a tissue or cell. Relative levels are generally measured vis-à-vis "normal" (i.e., non-cancerous) epithelial cells. Also, in all of these assays the cell expresses BRCA1 mRNA.

In all of these assays, the levels of mi-RNA in the cell of interest can be measured by any method known in the art. Such methods include, without limitation, quantitative or semi-quantitative RT-PCR methodologies employing appropriate miR-182-specific oligonucleotide primers and hybridization assays using detectably labeled miR-182-specific DNA or RNA probes. Additional methods for quantitating miR-182 in cell lysates include RNA protection assays and small Northern blots. Alternatively, qualitative, quantitative, or semi-quantitative in situ hybridization assays can be carried out using, for example, tissue sections or unlysed cell suspensions, and detectably (e.g., fluorescently or enzyme) labeled DNA or RNA probes.

The assays can be performed using a tissue or a cell that is suspected of being cancerous. The assays can also be performed using a tissue or a cell from a patient undergoing routine screening who is not known or suspected to have cancer. The tissue or cell can be obtained from, e.g., a biopsy sample or a blood sample of the individual. In performing the assay, the level of the miR-182 in the cell of interest may be compared to a control tissue or cell. The control tissue or cell is non-cancerous and is generally of the same type as the cell being assayed. In some embodiments, the control cell is a normal (i.e., non-cancerous) cell from the subject from whom the tissue or a cell that is suspected of being cancerous is obtained. In most instances, the control cell is generally an epithelial cell from the same organ/tissue as the cell being assayed. For example, if a breast epithelial tissue/cell is being assayed, a corresponding non-cancerous breast epithelial tissue/cell may be used as a control; if a prostate epithelial cell is being assayed, the control cell can be a normal prostate epithelial cell; and if an ovarian epithelial tissue/cell is being assayed, a corresponding non-cancerous ovarian epithelial tissue/cell can be used as a control. The control cell/tissue may be, but is not required to be from the same individual. In fact, in some instances, the control cell/tissue is provided from a different individual who is established or known to not have the specific cancer being assayed. In certain embodiments, the control tissue or cell is sex-matched, age-matched, and/or race-matched to the individual whose cell or tissue is being assayed. For example, if a 50 year old African-American female's cell or tissue is being assayed, the control cell should ideally be from an African American female who is between about 45 and about 55 years of age; and if a 60 year old Asian male's cell or tissue is being assayed, the control cell should ideally be from an Asian male who is between about 55 and about 65 years of age. In certain embodiments, the control may be the mean expression level (as a measure of the number of cells used) obtained from the expression levels of miR-182 from a number of individuals, wherein the same histological type as the cell being assayed is used to measure the miR-182 expression level, and wherein all of the individuals used to obtain the mean expression miR-182 expression level do not have cancer. In this case, the individuals may be from different age groups, races and sexes. Alternatively, the individuals may be from the same age groups, race and/or sex.

These assays are generally useful for detecting or diagnosing cancers including, but not limited to, breast cancer, ovarian cancer, prostate cancer, bladder cancer, testicular cancer, cervical cancer, uterine cancer, skin cancer (e.g., melanoma), pancreatic cancer, and colon cancer. In certain preferred embodiments, the cancer is breast or ovarian cancer. In specific embodiments, the cancer is sporadic breast cancer. In other specific embodiments, the cancer is estrogen receptor-negative sporadic breast cancer.

In assays for determining the level of BRCA1 in a tissue or cell, the level of miR-182 is measured in the tissue or cell. This level may then be compared to a control tissue or cell. If the level of miR-182 in the tissue or cell is higher than the level of miR-182 in the control tissue or cell, the tissue or cell is determined to have a lower level of BRCA1 relative to the control tissue or cell. Conversely, if the level of miR-182 in the tissue or cell is lower than the level of miR-182 in the control tissue or cell, the tissue or cell is determined to have a higher level of BRCA1 relative to the control tissue or cell. In the case of breast cancer cells, the control cell may be a normal (i.e., non-cancerous) human mammary epithelial cell (HMEC). HMECs can be obtained from the American Type Culture Collection, Manassas, Va. (e.g., ATCC No. CRL-10317™). The levels of miR-182 in an HMEC are considered to be "normal." Levels higher than the levels of miR-182 in an HMEC are considered "high," whereas levels lower than the levels of miR-182 in an HMEC are considered to be "low." High levels of miR-182 correspond to low levels of BRCA1 and vice versa.

An alternative to the above approach includes comparing the level of miR-182 in the cell at issue to a control level that is known or previously determined to correspond to a level in a non-cancerous cell or tissue of the same histological type as the cell/tissue being assayed. The same histological type means that the same cell type as the cell being assayed is used—i.e., if an epithelial cell is being assayed, the control level is determined from an epithelial cell (e.g., if a breast epithelial cell is being assayed, the control level is obtained from a non-cancerous breast epithelial cell; if an ovarian epithelial cell is being assayed, the control level is obtained from a non-cancerous ovarian epithelial cell). The control levels may be generated using a collection of cellular samples by creating a standard curve of BRCA1 levels plotted against miR-182 levels. Control levels can be established for different cell types (e.g., breast, ovary, prostate, colon, etc.) where the levels of miR-182 are plotted against the levels of BRCA1. This can be done using both normal (i.e., noncancerous) cells as well as using malignant cells at different stages of cancer. The curves can be created for different numbers of cells so as to determine the expression/number of cell. The curve generated from these standards can then be used to determine the level of BRCA1 in a test subject by simply measuring the miR-182 levels by qPCR and using the standard curves (adjusted, of course, for the number of cells used).

In some cases, a relative level of BRCA1 is measured. High levels of miR-182 corresponds to low levels of BRCA1 and vice versa. In the case of breast cancer cells, the standard to which the level human mammary epithelial cell (HMEC)

This assay can also be useful to determine the efficacy of anti-cancer treatments that are directly or indirectly directed to increasing levels of BRCA1. In such treatments, the levels of miR-182 may serve as a marker for the efficacy of the anti-cancer treatment: if the miR-182 levels in post-treatment cells are lower than the levels of miR-182 in pre-treatment cells, the treatment is deemed to be effective.

This invention also features assays for determining the likelihood that an individual will develop cancer. The assay involves measuring the levels of miR-182 in a cell or tissue of the individual. This level may then be compared to a control tissue or cell from an individual without cancer. If the level of miR-182 in the tissue or cell is higher than the level of miR-182 in the control tissue or cell, the individual is determined to have a higher likelihood of developing cancer than the individual from whom the control tissue or cell was obtained. Conversely, if the level of miR-182 in the tissue or cell is lower than the level of miR-182 in the control tissue or cell, the individual is not determined to have a higher likelihood of developing cancer than the individual from whom the control tissue or cell was obtained. Instead of comparing the level to a control tissue or cell from an individual without cancer, the level may be compared to a level that is known or previously determined to correspond to a level in a corresponding non-cancerous cell or tissue.

The invention also features assays for determining the prognosis of a patient having a cancer expressing high or comparable levels of BRCA1 mRNA relative to a corresponding non cancerous cell or tissue. The assay involves measuring the level of miR-182 in at least one cell of the patient and comparing this level to a control tissue or cell from an individual without cancer, or to a level that is known or previously determined to correspond to a level in a corresponding non-cancerous cell or tissue. The cell(s) for the assay is provided from the organ or tissue of the patient that is known to have cancer, or from an organ or tissue of the patient to which the cancer is thought to have spread. The patient is determined to have a poor prognosis if the level of miR-182 in the sample is higher than the level of miR-182 in a corresponding control sample. In contrast, the patient is determined to have a good prognosis if the level of miR-182 in the sample is the same or lower than the level of miR-182 in a corresponding control sample obtained from an individual without cancer.

It is noted that the assays described above need not be limited to assays of cells or tissues of human patients. They can also be performed from cells or tissues of other mammals, e.g., non-human primates (e.g., monkeys), horses, sheep, cattle, goats, pigs, dogs, guinea pigs, hamsters, rats, rabbits or mice.

These assays can be used to isolate from a population of individuals, those individuals that have a higher likelihood than the general population to develop a cancer. In addition, these assays can assist in classifying patients based on prognosis. Additionally, these assays can help in determining the impact of anti-cancer treatments on disease progression. The results of the assays conducted herein can be recorded on any medium (e.g., a computer readable medium).

Methods of Choosing Appropriate Cancer Treatments

Cancers result from the abnormal division of cells without control. There are many different treatments for cancers such as chemotherapy, radiation therapy, cryosurgery, laser treatment, gene therapy, angiogenesis inhibitor therapy, interferon therapy, interleukin therapy, monoclonal antibody therapy, and vaccination. One of the major problems with cancer treatments is the lack of specificity—i.e., the fact that the therapeutic agents kill and/or decrease proliferation of not only cancer cells but also healthy dividing cells. Accordingly, research has focused on targeted treatments that can selectively kill and/or decrease proliferation of just the cancerous cells/tissues. Among the recent drugs that have show great promise in that direction are the "PARP inhibitors."

A PARP inhibitor is a drug that blocks Poly (ADP-ribose) polymerase (PARP) proteins from performing their functions in cells. There are sixteen or more known PARPs (e.g., PARP1, PARP2, etc.). PARP1 inhibitors include, but are not limited to, 4-Amino-1,8-naphthalimide (ANI), ABT-888, KU59436, AZD2281/Olaparib, AG014699, BSI-201, INO-1001, and GPI 21016). As these PARP1 inhibitors are also likely to inhibit other PARPs, these inhibitors are referred to as PARP inhibitors. PARP is a protein that has several roles in cellular processes, most notably in DNA repair and programmed cell death. Chemotherapy and radiation work by damaging the DNA of cells. Just as healthy cells use PARP to repair DNA damage and live out their normal life cycle, cancer cells can use PARP to repair DNA damage and recover from the assault of cancer treatments. Such cancers can then become resistant to most cancer treatments. Agents that act as inhibitors of PARP effectively disarm the ability of cancer cells to repair themselves and cause the death of those cells. Importantly, while PARP inhibition kills cancer cells, it spares identical normal cells that lack cancer-related alterations.

The PARP inhibition strategy relies on the principle of "synthetic lethality." Two genes are said to be in a synthetic lethal relationship if a mutation in either gene alone is not lethal but mutations in both cause the death of a cell. In cells that carry BRCA1 and BRCA2 mutations, one of the two major DNA repair methods, known as homologous recombination, is nonfunctional. However, the other major repair method, known as base-excision repair, compensates for that loss. PARP-1 inhibition disables that base-excision repair. Thus, the PARP-1 enzyme is a target that, once hit and inhibited, leads to cell death.

The invention is based in part on the finding that cancer patients with BRCA1 and BRCA2 mutations are not the only candidates for PARP-1 inhibition: PARP-1 inhibition can also be effective in cancer patients with low levels of BRCA1 mRNA. As noted earlier, accurately determining the levels of BRCA1 in a cell is challenging. Accordingly, alternate methods of determining BRCA1 levels are required in order to determine whether a patient will benefit from PARP therapy. Determining miR-182 levels in a cell provides a method of assessing the relative levels of BRCA1 levels in a test sample compared to control non-cancerous cells. Accordingly, in order to determine whether a patient having cancer may benefit from PARP therapy the level of miR-182 is measured in a sample provided from the patient. This method may be applied to any cancer where BRCA1 mRNA levels are deregulated, including, but not limited to, breast cancer, ovarian cancer, colon cancer, pancreatic cancer, prostate cancer, testicular cancer, cervical cancer, uterine cancer, skin cancer (e.g., melanoma), leukemia, and lymphoma. In one preferred embodiment, the cancer is estrogen receptor-negative breast cancer. The sample to be analyzed may be obtained from e.g., a biopsy or a blood sample. The level of miR-182 can be measured by any method known to one of skill in the art. In preferred embodiments, the level of miR-182 is measured by quantitative RT-PCR. The patient is determined to benefit from PARP therapy if the level of miR-182 in the sample provided from the patient is higher than a control sample. Conversely, the patient is deemed to not benefit from PARP therapy if the level of miR-182 in the sample provided from the patient is lower than a control sample. The control tissue or cell that is used in this method is non-cancerous and is of the same type as the cell being assayed. The control tissue or cell may be from the same individual being tested or from a different individual. In most instances, the control cell is an epithelial cell from the same organ/tissue as the cell being assayed. Ideally the control tissue or cell is sex-matched, age-matched, and race-matched to the individual whose cell or tissue is being assayed. In certain cases, level of miR-182 in the sample is compared to a control level. The control level is a level of miR-182 in the same number of non-cancerous cells as the number of cells from the patient's sample and from the corresponding tissue/organ from which the cells of the patient's sample are isolated.

The disclosure also features methods of selecting the most appropriate form of chemotherapy in a patient undergoing cancer treatment. Some chemotherapeutic agents work most effectively in the absence of BRCA1 or when the levels of BRCA1 are low in the cancer cell being targeted. In contrast, other chemotherapeutic agents act most efficiently when BRCA1 is present at normal levels in a cancer cell. Thus, determining the level of BRCA1 in a cell can determine the nature of the chemotherapeutic treatment to be used for treating the cancer. The method of determining treatment of a patient with cancer involves measuring the levels of miR-182 in one or more cells of a sample from the patient. This method may be applied to any cancer where BRCA1 mRNA levels are deregulated, including, but not limited to, breast cancer, ovarian cancer, colon cancer, pancreatic cancer, prostate cancer, testicular cancer, cervical cancer, uterine cancer, skin cancer (e.g., melanoma), leukemia, and lymphoma. In one preferred embodiment, the cancer is estrogen receptor-negative sporadic breast cancer.

If the level of miR-182 is determined to be higher than a level of miR-182 in a control sample or higher than a control level, the patient is identified as a suitable candidate for treatment with a chemotherapeutic agent that is effective against cancers expressing low levels of BRCA1. Such chemotherapeutic agents include, but are not limited to, an alkylating agent (e.g. busulfan, chlorambucil, cisplatin, cyclophosphamide (cytoxan), dacarbazine, ifosfamide, mechlorethamine (mustargen), and melphalan), a topoisomerase inhibitor, an antimetabolite (e.g. 5-fluorouracil (5-FU), cytarabine (Ara-C), fludarabine, gemcitabine, and methotrexate), an anthracycline, an antitumor antibiotic (e.g. bleomycin, dactinomycin, daunorubicin, doxorubicin (Adriamycin), and idarubicin), an epipodophyllotoxin, and nitrosureas (e.g. carmustine and lomustine). Non-limiting examples of chemotherapeutic agents that are effective against cancers expressing low levels of BRCA1 include topotecan, irinotecan, doxorubicin, etoposide, mitoxantrone, bleomycin, busultan, mitomycin C, cisplatin, carboplatin, oxaliplatin and docetaxel.

If the level of miR-182 is determined to be lower than a level of miR-182 in a control sample or lower than a control level, the patient is identified as a suitable candidate for treatment with a chemotherapeutic agent that is effective against cancers expressing normal or high levels of BRCA1. Such chemotherapeutic agents include, but are not limited to mitotic inhibitors such as spindle poisons. Spindle poisons are well known to the ordinary skilled artisan and include taxanes and vinca alkaloids among others. Non-limiting examples of chemotherapeutic agents that are effective against cancers expressing high levels of BRCA1 include paclitaxel, vincristine, vinblastine, vinorelbine, vindesine, and epirubicin.

Methods of Modulating Expression of BRCA1 and Methods of Treatment

The microRNAs and antagomirs described herein can also be used in the treatment of subjects to ameliorate symptoms associated with a disease or condition, prevent or delay onset of disease symptoms, and/or lessen the severity or frequency of symptoms of the disease.

miR-182 or variants thereof can be administered to a cell to decrease the levels of BRCA1. The cell may be ex vivo or in vivo. An in vivo administration of miR-182 or variants thereof is helpful in combination therapy with other agents, for example, in treating a patient with PARP inhibitors or genotoxic agents. As described above, PARP inhibitors inhibit PARP, a protein that is involved in DNA repair. If PARP is inhibited at the same time that BRCA1, which is also involved in DNA repair, is reduced in a cancer cell, PARP inhibitors will be more effective in targeting the cancer cell. This is, in part, because the damage caused by inhibiting PARP will not be rescued by BRCA1. Non-limiting examples of PARP inhibitors include 4-Amino-1, 8-naphthalimide (ANI), ABT-888 (Abbot Labs), KU59436 (AstraZeneca), AZD2281/Olaparib (Astra-Zeneca), AG014699 (Pfizer), BSI-201 (BiPar), INO-1001 (Genentech), and GPI 21016 (MGI Pharma). The combination therapy of PARP inhibition and miR-182 mediated BRCA1 downregulation can be more effective than PARP inhibitor therapy alone.

Lowering BRCA1 levels by administering miR-182 can also improve treatment of a patient with a genotoxic agent. The genotoxic agent can be a chemotherapeutic agent or radiotherapeutic agent. Non-limiting examples chemotherapeutic agents include carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gencitabine, cisplatin (CDDP), adriamycin (ADR), and analogs thereof. Genotoxic agents also include gamma-radiation, X-irradiation, infrared-radiation, UV-radiation, and beta-radiation. The reduction in levels of the DNA repair protein BRCA1, prevents the cancer cell that is being treated with a genotoxic agent from repairing the damage inflicted by the genotoxic agent and surviving the assault. These methods are especially advantageous because they only target cells having low levels of BRCA1 without harming surrounding normal cells.

These methods are useful in treating any cancer in which BRCA1 mRNA is expressed and particularly, in treating any cancer where the levels of BRCA1 mRNA are higher than the levels in a normal cell from the same tissue. Non-limiting examples of cancers that can be treated by these methods include breast cancer, ovarian cancer, prostate cancer, testicular cancer, cervical cancer, uterine cancer, pancreatic cancer, skin cancer, colon cancer, leukemia, lymphoma, and melanoma. In the context of breast cancer treatment, administration of miR-182 along with either PARP therapy or genotoxic agents is most beneficial when the patient has an ER-negative sporadic breast cancer. miR-182 or variants thereof may be administered to the subject prior to, at the same time as, or after treatment with PARP inhibitors or genotoxic agents. In some instances, miR-182 or variants thereof may be administered both before and after, before and at the same time as, or at the same time as and after treatment with the PARP inhibitors or genotoxic agents.

In certain circumstances, it may be desirable to increase the levels of BRCA1 in a cell. In such cases the cell is administered with an antagomir of miR-182 or variants thereof. Increasing BRCA1 levels may be helpful for example in patients whose DNA repair machinery is faulty or in situations where certain chemotherapeutic agents need normal or high levels of BRCA1 (compared with a non cancerous cell) to function effectively. Mitotic inhibitors such as spindle poisons require BRCA1 to be present in order to be effective. Non-limiting examples of spindle poisons include taxanes and vinca alkaloids. In specific embodiments, the spindle poison is one of: paclitaxel, vincristine, vinblastine, vinorelbine, and vindesine. The miR-182 antagomirs or variants thereof may be administered to the subject prior to, at the same time as, or after treatment with the spindle poison. In some instances, miR-182 antagomir or variants thereof may be administered both before and after, before and at the same time as, or at the same time as and after treatment with the spindle poison.

In certain embodiments, it is desired to kill cells, inhibit cell growth, inhibit metastasis, decrease tumor or tissue size, and/or reverse or reduce the malignant or disease phenotype of cells. The routes of administration will vary with the location and nature of the lesion or site to be targeted. Non-limiting routes of administration include: intradermal, subcutaneous, regional, parenteral, intravenous, intramuscular, intranasal, systemic, and oral administration. Direct injection, intratumoral injection, or injection into tumor vasculature is specifically contemplated for discrete, solid, accessible tumors, or other accessible target areas. Local, regional, or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as a single dose comprise about 0.1 ml to about 0.5 ml volumes. Compositions of the invention may be administered in multiple injections to a tumor or a targeted site. In certain aspects, injections may be spaced at approximately 1 cm intervals.

The microRNAs and antagomirs described herein may also be administered to a subject at the time of surgery, and/or thereafter, to treat residual or metastatic disease. For example, a resected tumor bed may be injected or perfused with a formulation comprising a miRNA or combinations thereof. Administration may be continued post-resection, for example, by leaving a catheter implanted at the site of the surgery. Periodic post-surgical treatment is also contemplated Continuous perfusion of an expression construct or a viral construct that encodes the miR-182 or antagomir of miR-182 is also envisioned.

Continuous administration may be used where appropriate, for example, where a tumor or other undesired affected area is excised and the tumor bed or targeted site is treated to eliminate residual, microscopic disease. Delivery of the microRNAs or antagomirs described herein via syringe or catherization is contemplated. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Liposomes can also be used to deliver the microRNAs and antagomirs described herein (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes are well known in the art. The liposomes for use in the present methods can comprise a ligand molecule that targets the liposome to cancer cells, e.g., ligands that bind to receptors prevalent in cancer cells, such as monoclonal antibodies that bind to tumor cell antigens. The liposomes can also be modified so as to avoid clearance by the mononuclear macrophage system and reticuloendothelial system. Such modified liposomes have opsonization-inhibition moieties on the surface or incorporated into the liposome structure. In one embodiment, a liposome of the invention can comprise both an opsonization-inhibition moiety and a ligand. Opsonization-inhibiting moieties for use in preparing the liposomes of the invention are typically large hydrophilic polymers that are bound to the liposome membrane. These opsonization-inhibiting hydrophilic polymers form a protective surface layer that significantly decreases the uptake of the liposomes by the MMS and RES. Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include, but are not limited to polyethylene glycol (PEG) or polypropylene glycol (PPG) or derivatives thereof (e.g., methoxy PEG or PPG, and PEG or PPG stearate); synthetic polymers, such as polyacrylamide or poly N-vinyl pyrrolidone; linear, branched, or dendrimeric polyamidoamines; polyacrylic acids; polyalcohols (e.g., polyvinylalcohol and polyxylitol to which carboxylic or amino groups are chemically linked), as well as gangliosides, such as ganglioside GM1. Liposomes modified with opsonization-inhibition moieties remain in the circulation much longer than unmodified liposomes. Liposomes are known to accumulate in tissues fed by porous or "leaky" microvasculature. Thus, tissue characterized by such microvasculature defects, for example, solid tumors, will efficiently accumulate these liposomes. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the microRNAs and antagomirs described herein (or nucleic acids comprising sequences encoding them) to tumor cells.

Methods of administering the molecules described herein as well as treatment regimens may vary and will depend on the tumor type, tumor location, immune condition of the subject, target site, disease progression, and health and age of the subject. The clinician will be best suited to make such decisions based on the known efficacy and toxicity (if any) of the therapeutic formulations.

The miRNAs and antagomirs described herein can be administered to the subject in a dose or doses of about or of at least about 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1500, 2000, 2500, 3000 μg or mg, or any range between 0.5 μg or mg and 3000 μg or mg. The amount specified may be the amount administered as the average daily, average weekly, or average monthly dose, or it may be expressed in terms of mg/kg, where kg refers to the weight of the patient and the mg is specified above. In other embodiments, the amount specified is any number discussed above but expressed as $mg/m^2$ (with respect to tumor size or patient surface area). A clinician can readily determine the effective amount of a miR-182 or an antagomir of miR-182 to be used—i.e. the amount of these molecules needed to inhibit proliferation of a cancer cell, by taking into account factors, such as the size and weight of the subject; the extent of disease penetration; the age, health and sex of the subject; the route of administration; and whether the administration is regional or systemic.

Kits and Articles of Manufacture

The disclosure also features a variety of kits. The kits can include one or more of: miR-182, miR-182 variants, antagomirs of miR-182, miR-182 antagomir variants; expression vectors containing nucleic acid sequences encoding miR-182, one or more miR-182 variants, or one or more variants of miR-182 antagomirs; reagents for isolating miRNA; reverse transcriptase; reagents for amplifying nucleic acids (e.g. primers to amplify miR-182); reagents for preparation of samples from blood samples or biopsy samples; nuclease free water; RNAse free containers; RNase-free tube tips; and RNase inhibitors. In addition, the kits can contain instructions for administering the miR-182 or antagomir of miR-182 to a subject. The instructions may be present in the kits in a variety of forms, e.g., as printed information on a suitable medium or substrate, a computer readable medium, or a website address that may be used via the internet to access the information. The kit can include one or more pharmaceutically acceptable carriers. In addition, devices or materials for administration of the microRNAs or antagomirs (e.g., syringes (pre-filled with miR-182 or antagomirs of miR-182), needles, liposomes, etc.) can also be included.

The kits can also contain one or more therapeutic agents, diagnostic agents, or prophylactic agents. The one or more therapeutic, diagnostic, or prophylactic agents include, but are not limited to: (i) a PARP inhibitor (e.g., 4-Amino-1,8-naphthalimide (ANI), ABT-888 (Abbot Labs), KU59436 (AstraZeneca), AZD2281/Olaparib (Astra-Zeneca), AG014699 (Pfizer), BSI-201 (BiPar), INO-1001 (Genentech), and GPI 21016 (MGI Pharma)); (ii) a genotoxic agent (e.g., chemotherapeutic agents such as, but not limited to, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gencitabine, cisplatin (CDDP), adriamycin (ADR), and any analogs thereof); (iii) a spindle poison (e.g., a taxane or vinca alkaloid, such as, paclitaxel, vincristine, vinblastine, vinorelbine, and vindesine); and (iv) cytoprotectants such as a radiosensitiser (e.g., vitamin K mimetics such as Synkavit or Menadione, gadolinium texaphyrin or iobenguane); a chemoprotectant (e.g., Sulcraphate, cysteine, cysteamine, Ethyol, Balazipone or dosmalfate); a free-range scavenger (e.g., WR 3689 (2-[[3-methylamino)propyl]amino]ethanediol dihydrogen phosphate ester, AD 20 (2-[[2-methoxyphenyl)acetyl]amino]-2-propenoic acid or nitroxide antioxidant); a growth factor (e.g., granulocyte colony-stimulating factor (G-CSF), granulocyte-macrophage colony-stimulating factor (GM-CSF), Erythropoietin (EPO), epidermal growth factor (EGF), keratinocyte growth factor (KGF), transforming growth factor (TGF- and -β); any interleukin (IL) including, IL-1 through IL-35, insulin-like growth factor (IGF), nerve growth factor (NGF), platelet derived growth factor (PDGR), Bombesin, Relaxin, Calcitonin, colostrum-derived growth factor (CDGF), amlexanox or amoxanox, protegrin, pilocarpine hydrochloride, stem cell factor (STF), thrombopoietin, steel factor (SF), any interferon, including interferon or any cytokine), or a combination of two or more thereof.

In some embodiments, the kits can contain one or more sets of primers for miR-182, any known target of miR-182 regulation (e.g., FOXO3, microphthalmia-associated transcription factor-M), BRCA1, or any target gene of BRCA1 (e.g., GADD45). The kits can optionally include instructions for assaying a biological sample for the presence or amount of one or more of miR-182 and BRCA1.

The invention also features articles of manufacture that include: a container; and a composition contained within the container, wherein the composition comprises a set of primers to measure miR-182 levels. The primers may be lyophilized or in suspension. If lyophilized, the article of manufacture may also contain a container containing sterile water or buffered saline. The container may include a label indicating that the composition is for use in measuring the levels of miR-182 and/or BRCA1. The article of manufacture may also contain a container containing one or more PARP inhibitors.

Other articles of manufacture that are featured include: a container; and a composition contained within the container, wherein the composition comprises an active ingredient for downregulating BRCA1 in a mammal (e.g., a human), wherein the active ingredient comprises miR-182 or any miR-182 variants, and wherein the container has a label indicating that the composition is for use in downregulating BRCA1 in a mammal (e.g., any of the mammals described herein). The label can further indicate that the composition is to be administered to a mammal having, suspected of having, or at risk of developing, cancer (e.g., breast cancer, ovarian cancer, colon cancer, pancreatic cancer, prostate cancer, testicular cancer, cervical cancer, uterine cancer, leukemia, lymphoma, and/or melanoma) in combination with PARP inhibitors or chemo- or radio-therapy. The composition of the article of manufacture can be dried or lyophilized and can include, e.g., one or more solutions (and/or instructions) for solubilizing a dried or lyophilized composition. The container is preferably nuclease, and in particular, RNase free.

Other articles of manufacture that are featured include: a container; and a composition contained within the container, wherein the composition comprises an active ingredient for upregulating BRCA1 in a mammal (e.g., a human), wherein the active ingredient comprises an antagomir of miR-182 or any miR-182 antagomir variants, and wherein the container has a label indicating that the composition is for use in upregulating BRCA1 in a mammal (e.g., any of the mammals described herein). The label can further indicate that the composition is to be administered to a mammal having, suspected of having, or at risk of developing, cancer (e.g., breast cancer, ovarian cancer, colon cancer, pancreatic cancer, prostate cancer, testicular cancer, cervical cancer, uterine cancer, leukemia, lymphoma, and/or skin cancer including melanoma) in combination with chemotherapeutic agents that require BRCA1 to be present at normal or high levels to act effectively. The composition of the article of manufacture can be dried or lyophilized and can include, e.g., one or more solutions (and/or instructions) for solubilizing a dried or lyophilized composition. The container is preferably nuclease, and in particular, RNase free.

The articles of manufacture can also include instructions for administering the composition to the mammal (e.g., as described above).

The following examples are intended to illustrate, not limit, the invention.

EXAMPLES

Example 1

Materials and Methods

Cell Culture and Differentiation.

Figure 6:
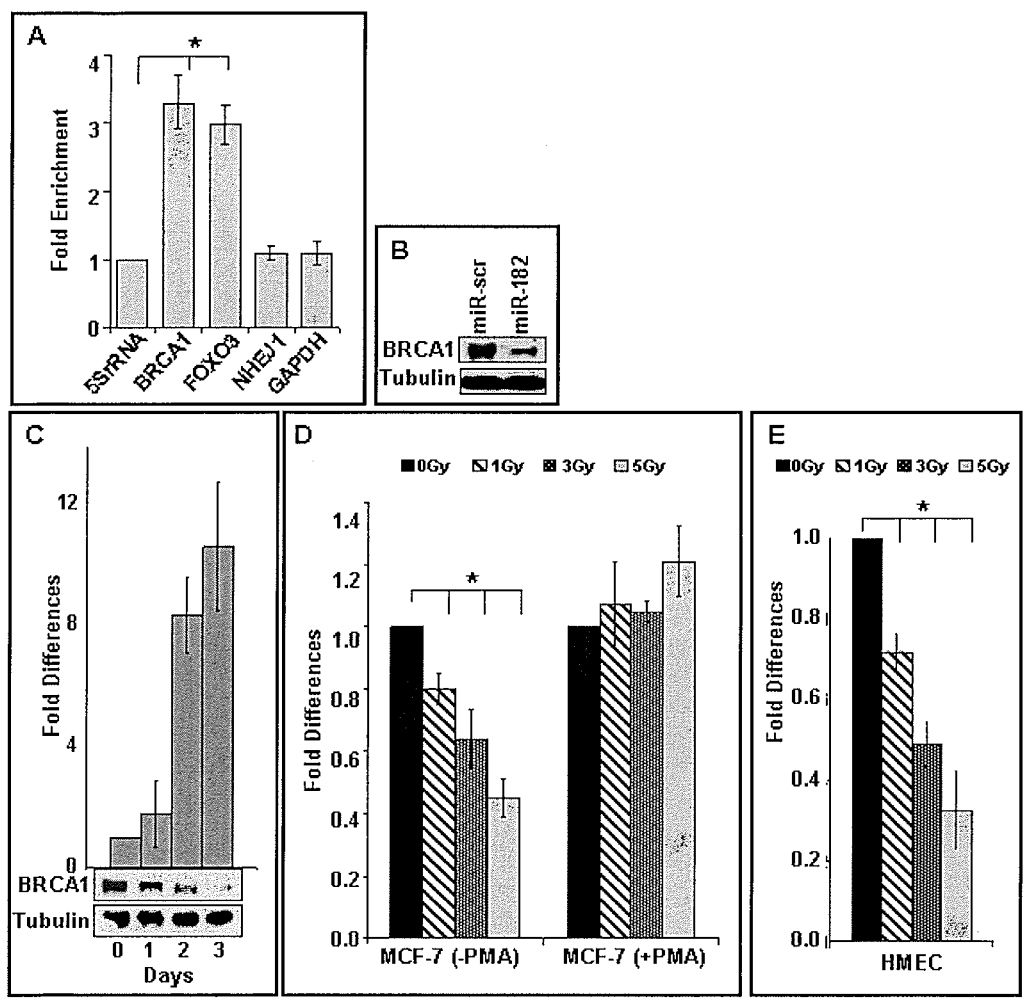
FIG. 6A is a bar graph showing the fold enrichment of transcripts associated with miR-182. MDA-MB231 cells were co-transfected with expression vectors for HA-tagged AGO1 and miR-182, respectively. The immunoprecipitated RNA was analyzed by qRT-PCR using gene-specific primers and normalized to 5S rRNA. FOXO3 (*p<0.002) and GAPDH served as positive and negative controls, respectively. BRCA1 (*p<0.002) but not NHEJ1, was significantly enriched in the pull-down. Mean±SD, n=3 independent experiments.
FIG. 6B is a photograph of a Western blot, which shows that miR-182 down regulates BRCA1 protein levels in breast cancer cell lines. MDA-MB231 cells transiently transfected with an expression vector encoding miR-182 and control (miR-scr) were harvested and cell lysates analyzed by immunoblot after normalization for total protein using anti-BRCA1 antibody or anti-tubulin antibody.
FIG. 6C is a bar graph showing the kinetics of miR-182 expression compared with a photograph of a western blot of BRCA1 protein levels during TPA-induced differentiation of MCF7 cells. miR-182 was quantified by qRT-PCR normalized to RNU6B. Mean±SD, n=3 independent experiments, p<0.0091. anti-tubulin antibody was used as a loading control.
FIG. 6D is a bar graph showing that miR-182 is rapidly downregulated with γ-radiation in proliferating MCF7 breast epithelial cells. Proliferating (left panel) or TPA-treated post-mitotic MCF7 cells (right panel) were exposed to indicated doses of IR and RNA was isolated 30 min after exposure. There was a significant reduction of miR-182 in MCF7 cells at 1 Gy (*p<0.007). The expression of miR-182 was analyzed with qRT-PCR and normalized to RNU6B and in all panels, mean±SD, n=3-6 independent experiments.
FIG. 6E is a bar graph showing that miR-182 is rapidly downregulated with γ-radiation in proliferating HMEC breast epithelial cells. Proliferating HMEC cells were exposed to the indicated doses of gamma irradiation and RNA was isolated 30 min after exposure. There was a significant reduction of miR-182 in HMEC cells at 1 Gy (*p<0.005). The expression of miR-182 was analyzed with qRT-PCR and normalized to RNU6B and in all panels, mean±SD, n=3-6 independent experiments.
Figure 10:
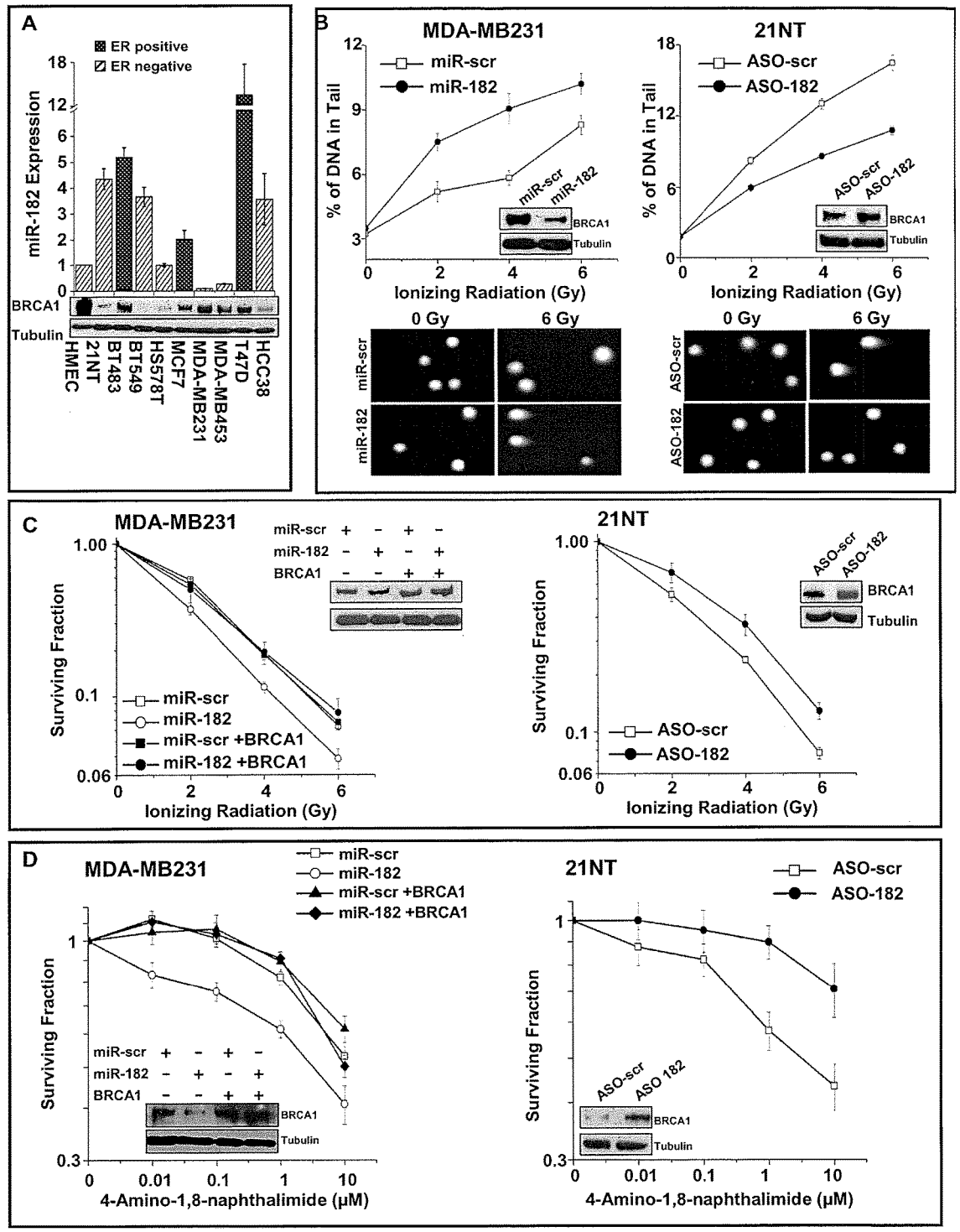
FIG. 10A provides a photograph of a Western blot of lysates from different breast cancer cell lines probed with anti-BRCA1 antibody and as a control, anti-tubulin antibody. The levels of miR-182 in these cell lines were quantified by qRT-PCR (normalized to RNU6) relative to the non-tumorigenic breast epithelial cell, HMEC, and is shown in a bar graph in the upper panel. Mean±SD, n=3 independent experiments. The estrogen receptor (ER) expression status of the different tumor lines is indicated.
FIG. 10B provides line graphs and photographs showing the effect of altering miR-182 levels on the amount of unrepaired double stranded breaks (DSBs) by comet assay in ER-negative tumor cells. MDA-MB231 cells (left panel) were transfected with either control mimic (miR-scr) or miR-182 mimic (miR-182). In addition, 21NT cells (right panel) were transfected with antagomirs (ASO), either control (AS0-scr) or ASO-182. Transfected cells were irradiated at the indicated doses, allowed to repair for 18 h and analyzed by single-cell gel electrophoresis (comet assay). BRCA1 protein is compared to tubulin levels in the immunoblots. Representative images are shown in the upper panel. Residual DNA damage after irradiation is significantly altered in 182 mimic (miR-182, p<0.001) or ASO-182 (p<0.001) transfected cells.
FIG. 10C is a series of line graphs showing the impact of miR-182 expression on the effect of ionizing radiation on cell viability in breast cancer cell lines. MDA-MB231 cells (left panels) were transfected with either control mimic (miR-scr) or miR-182 mimic (miR-182) or BRCA1 cDNA lacking the 3'UTR or both. Conversely, 21NT cells (right panels) were transfected with either control antagomir (ASO) or 182 ASO. Cell viability was assayed by clonogenic cell survival assay after indicated doses of γ-radiation. The line graphs were generated from 3 independent experiments. miR-182 mimic significantly enhanced sensitivity to IR (p<0.004), whereas miR-182 ASO reduced sensitivity to IR (p<0.001). The insets show representative immunoblots using lysates from the transfected cells probed with anti-BRCA1 antibody and anti-tubulin antibody.
FIG. 10D is a series of line graphs showing the impact of miR-182 expression on PARP1-mediated inhibition of cell viability in breast cancer cell lines. MDA-MB231 cells (left panels) were transfected with either control mimic or 182 mimic or BRCA1 cDNA lacking the 3'UTR or both. Conversely, 21NT cells (right panels) were transfected with either control antagomir (ASO) or 182 ASO. Cell viability was assayed by clonogenic cell survival assay after exposure of cells to PARP1 inhibitor (ANI) at indicated concentrations. The line graphs were generated from 3 independent experiments. miR-182 mimic significantly enhanced sensitivity to ANI (p<0.001), whereas miR-182 ASO reduced sensitivity to ANI (p<0.002). The insets show representative immunoblots using lysates from the transfected cells probed with BRCA1 and tubulin antibodies.

HL60 cells ($0.5 \times 10^6$ cells/ml) were differentiated either to neutrophils with 1.3% DMSO for 8 days or to macrophages with 16 nM tetradecanoyl phorbol acetate (TPA) for 3 days; K562 cells ($0.5 \times 10^6$ cells/ml) to megakaryocytes with 16 nM phorbol myristate acetate (PMA) for 3 days or to erythrocytes with 100 mM Hemin for 4 days. HL60 and K562 cells were grown in DMEM or RPMI-1640, respectively, supplemented with 10% (v/v) FBS. MCF-7 cells ($10^6$ cells/6 cm dish) were differentiated with 100 nM TPA for 3 days in Dulbecco's Modified Eagle Medium (DMEM) with 10% (v/v) fetal bovine serum (FBS) (Cunliffe et al., *Cancer Res.*, 63:7158-66 (2003). The breast cancer lines and human mammary epithelial cells used in experiments shown in FIGS. 6 and 10, were cultured in media according to protocols from the American Type Culture Collection (ATCC®; Manassas, Va.) (www.atcc.org/).

miRNA Microarray, RNA Isolation and Quantitative PCR.

K562 ($0.5 \times 10^6$ cells/ml) were terminally differentiated to megakaryocytes with 16 nM TPA for 3 days. Undifferentiated and differentiated K562 cells were untreated or exposed to 2 Gy of gamma radiation. Total RNA was extracted with Trizol reagent (Invitrogen, Carlsbad, Calif.) according to manufacturer's manual and treated with 10 U DNase I for 30 minutes at 37° C. in 50 µl. RNAse-free water (250 µl) was added and DNase I removed with 300 µl acid phenol-choloroform (Ambion, Austin, Tex.). The TaqMan Human MicroRNA Array v 1.0 (Early Access) platform which is qPCR based method was used for quantitative miRNA analysis and was carried out in Dana-Farber Cancer Institute core facility.

Analysis of the miRNAs of the miR-183 cluster was conducted using qPCR using the TaqMan MicroRNA Assay from Applied Biosystems as per the manufacturer's instructions and normalized to RNU6B snRNA. Analysis of mRNA expression was carried out with qPCR using the SYBR Green master mix (Applied Biosystems, Foster City, Calif.) according to the manufacture's manual and the BioRad iCycler. The mRNA (1 µg) was reverse transcribed with 50 ng random primers using 100 U moloney murine leukemia virus (MMLV) reverse transcriptase (Epicentre, Madison, Wis.) according to the manufacturer's manual. Results were normalized to 5SrRNA or GAPDH.

Gene Specific Primers (F=Forward; R=Reverse):

```
BRCA1
F: CAACATGCCCACAGATCAAC        (SEQ ID NO: 9)
R: ATGGAAGCCATTGTCCTCTG        (SEQ ID NO: 10)

NHEJ1
F: AGTGCCAAGTGAGGGAGCTA        (SEQ ID NO: 11)
R: CCACTTGGACCTCTTGTGT         (SEQ ID NO: 12)

FOXO3
F: GATAAGGGCGACAGCAACAG        (SEQ ID NO: 13)
R: CCAGTTCCCTCATTCTGGAC        (SEQ ID NO: 14)

5S rRNA
F: GCC CGA TCT CGT CTG ATC T   (SEQ ID NO: 15)
R: AGC CTA CAG CAC CCG GTATT   (SEQ ID NO: 16)
```

-continued

```
GAPDH
F: TGCACCACCAACTGCTTAGC              (SEQ ID NO: 17)
R: GGCATGGACTGTGGTCATGAG             (SEQ ID NO: 18)

FNDC3A
F: CTTGGAGCTGGTCCTTTCAG              (SEQ ID NO: 19)
R: CCTTCCCCAGCTTCATTACA              (SEQ ID NO: 20)
```

Algorithm Tools to Predict Targets of miR-183 Cluster.

The RNA22 algorithm (cbcsrv.watson.ibm.com/rna22_targets.html) was used to find targets of miR-182. The 3'UTR of BRCA1 was further analyzed by RNAhybrid (bibiserv.techfak.uni-bielefeld.de/rnahybrid/) and PITA algorithm (genie.weizmann.ac.il/pubs/mir07/mir07_prediction.html).

Immunoprecipitation of miR-182 and miR-17 Targets.

miR-182 cDNA and miR-17 cDNA was cloned from HL60 cDNA in pcDNA3.1-Puro expression vector (Invitrogen, Carlsbad, Calif.) using the following primers:

```
miR-182
                                     (SEQ ID NO: 21)
F: CGGCGGCCGCGATATGAGGGGAAGGGAGGA
                                     (SEQ ID NO: 22)
R: CGGCGGCCGCGAGAAGGTTCACCACCCAGA miR-17
                                     (SEQ ID NO: 23)
F: ATAAGCTTCATTGGAAGAGCCACCACTTC
                                     (SEQ ID NO: 24)
R: ACTCGAGTTGCTTGGCTTGAATTATTGG
```

MDA-MB231 cells ($0.5 \times 10^6$ cells) were co-transfected with 1 μg of HA-AGO1 (pIRES-FLAG/HA vector, Addgene) and 0.5 μg of expression vector for miR-182/miR-17 or miR-scr using Lipofectamine 2000. After 2 days cells were harvested using 400 μl lysis buffer (100 mM KCl, 5 mM $MgCl_2$, 10 mM Hepes, pH 7.0, 0.5% Nonidet P-40) containing freshly added RNase inhibitor, RNaseOUT (Invitrogen, Carlsbad, Calif.) and Protease Inhibitor Cocktail (Roche, Basel, Switzerland). After centrifugation, a 50 μl aliquot of supernatant was taken as the input for subsequent RNA extraction. The remaining supernatant was gently shaken with HA-beads (HA-probe Santa Cruz sc-7392) for 4 h at 4° C. in spin columns (Pierce Spin Columns-Screw Cap). The columns were drained, washed and the retained beads were treated with 5 U DNaseI in NT2 buffer (50 mM Tris, pH7.4, 150 mM NaCl, 1 mM $MgCl_2$, 0.05% Nonidet P-40) for 10 minutes at 37° C., washed with NT2 buffer and then treated with Proteinase K in NT2 buffer plus 1% SDS for 30 minutes at 55° C. Finally, the beads were re-suspended in NT2 buffer and RNA was extracted using acid phenol-choloroform (Ambion, Austin, Tex.). RNA was reverse transcribed (see RNA isolation) and analyzed with qPCR for enrichment of mRNA of miR-182/miR-17 predicted targets.

Luciferase Assay.

The wild type (WT) and mutated (M) miR-182 recognition elements of 3'UTR-BRCA1 were annealed (see below) and cloned in expression vector, pMIR-REPORT (Ambion, Austin, Tex.) downstream to Firefly Luciferase.

```
WT F:
                                     (SEQ ID NO: 25)
CTAGTAGAAGAGATTTCTAAAAGTCTGAGATATATTTGCTAGATTTCTA
AAGAATGTGTTCTAAAACAGCAGAAGATTTTCAAGAACCGGTTTCCAAA
GACAG

WT R:
                                     (SEQ ID NO: 26)
AGCTCTGTCTTTGGAAACCGGTTCTTGAAAATCTTCTGCTGTTTTAGAA
CACATTCTTTAGAAATCTAGCAAATATATCTCAGACTTTTAGAAATCTC
TT

M F (The mutant residues have been underlined.):
                                     (SEQ ID NO: 27)
CTAGAAGAGACGATACCCGTCTGAGATATATTTGCTAGGCGATACCCGG
GTGTGTTCTAAAACAGCAGAAGCCGATACCCGGCCGGCGATACCCGACA
G M R:
                                     (SEQ ID NO: 28)
AGCTCTGTCGGGTATCGCCGGCCGGGTATCGCTTCTGCTGTTTTAGAAC
ACACCCGGGTATCGCCTAGCAAATATATCTCAGACGGGTATCGCTCTCT
TCTAG
```

Hela cells were co-transfected in a 24 well tissue culture plate with 10 nM control mimic (Ambion, Austin, Tex.) or miR-182 mimic (Ambion, Austin, Tex.), 0.2 μg 3'UTR-BRCA1-WT or 3'UTR-BRCA1-M, and 0.2 μg Renilla luciferase in pRL-TK (Promega, Madison, Wis.) vector using lipofectamine 2000 as described in manufacture's manual. Cells were harvested on day 2 and the luciferase activity was assayed with the Dual-Luciferase Assay System (Promega, Madison, Wis.) and a Synergy HT microplate reader (BioTek, Winooski, Vt.) as described in manufacture's manual.

Immunoblots.

In each experiment, where Western blot analysis was done, a fraction of $0.2-0.5 \times 10^6$ cells was taken out at day, 3 or 4, post-transfection. Breast cancer cell lines were collected from 6 well tissue culture plates ($0.5-1 \times 10^6$ cells). Cells lysates were prepared in RIPA buffer (150 mM NaCl, 1% NP-40, 0.5% sodium deoxycholate, 0.1% SDS, 50 mM Tris, pH 8.0). Lysates of $0.1 \times 10^6$ cells of each sample plus loading buffer were loaded on 8% SDS-PAGE gels, semi-dry transferred on nitrocellulose membrane, and probed with anti-BRCA1 antibody at a 1:500 dilution (CALBIOCHEM, MS110) and anti-tubulin antibody at a 1:10,000 dilution (Sigma, Clone B-5-1-2).

PARP Activity Assay.

MDA-MB231 cells ($2 \times 10^6$) were plated in 10-cm tissue culture dishes overnight in duplicates. The cells were exposed to the indicated concentrations of 4-Amino-1,8-naphthalimide in phosphate buffered saline (PBS) for 10 minutes on ice followed by 100 μM $H_2O_2$ for 20 minutes on ice. The cells were then washed thrice in ice cold PBS for 8-10 minutes and incubated in complete medium with the indicated concentrations of 4-Amino-1,8-naphthalimide at 37° C. The cells were then lysed and PARP activity was measured using the universal PARP chemiluminescent assay kit (Trevigen, Gaithersburg, Md.) as per the manufacturer's instructions.

Single-Cell Gel Electrophoresis (Comet) Assay.

21NT cells ($0.35 \times 10^6$ cells/well in 6 well tissue culture plate) were transfected with 100 nM control or miR-182 antagomir expression vector (Ambion, Austin, Tex.) whereas MDA-MB231 ($0.35 \times 10^6$ cells/well on 6 well plate) were transfected with 10 nM control or miR-182 mimic expression vector (Ambion, Austin, Tex.) using Lipofectamine 2000. At day 3 after transfection, cells were irradiated (0, 2, 4 and 6 Gy) and allowed to recover for 18 hours prior to analysis. The single cell comet assays was carried out according manufacturer's instructions (Trevigen, Gaithersburg, Md.). Briefly, treated or untreated cells were collected, resuspended in ice cold PBS at $10^5$ cells/ml, mixed with low-melting point agarose (1:10 ratio) and spread on frosted glass slides. After the agarose solidified, the slides were placed in lysis buffer and then in alkaline solutions. Slides were then subjected to electrophoresis (1 V per cm of distance between electrodes) for 10 minutes in 1× TBE buffer, following which cells were fixed with 70% (v/v) ethanol and stained with DAPI. Nuclei were visualized using epifluorescent illumination on a Zeiss microscope and images analyzed with National Institutes of Health ImageJ software (rsbweb.nih.gov/ij/). DNA damage was quantified for 70-100 cells for each experimental condition by determining the DNA in the comet tail using the software Comet Score (TriTek, Sumerduck, Va.).

Homologous Recombination (HR) Reporter Assay.

Figure 3:
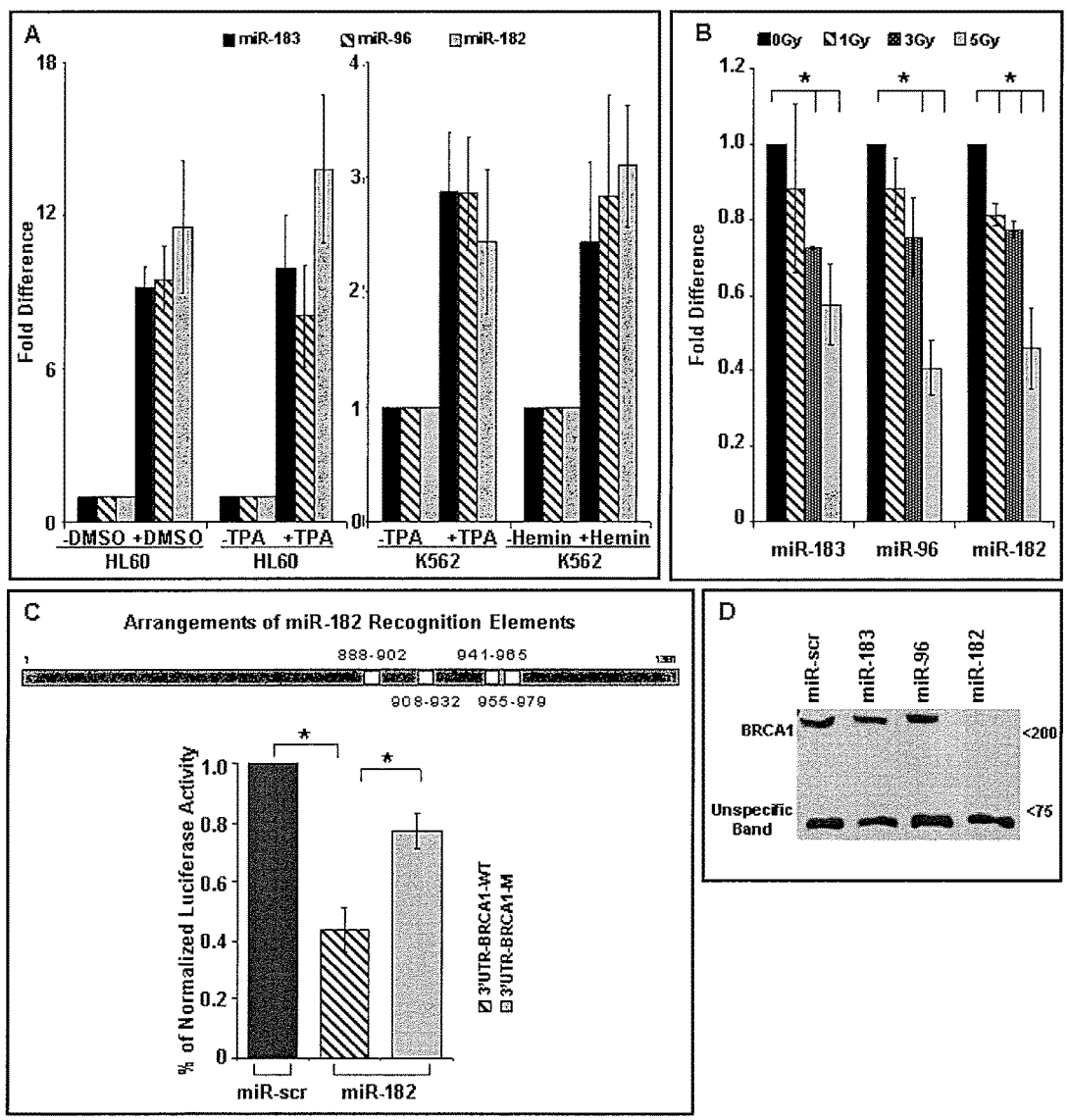
FIG. 3A is a bar graph depicting the expression of miR-183, miR-96 and miR-182 during differentiation of HL60 cells to neutrophils (dimethyl sulfoxide (DMSO), 8 days, p<0.001) and macrophages (TPA, 3 days, p<0.001); K562 cells to megakaryocytes (TPA, 3 days, p<0.002) and to erythrocytes (Hemin, 4 days, p<0.003).
FIG. 3B is a bar graph showing that miR-183, miR-96 and miR-182 are rapidly downregulated following γ-radiation in proliferating HL60 cells. There was significant reduction in miR-183 (p<0.002), miR-96 (*p<0.003) and miR-182 (*p<0.002) at 3 Gy.
FIG. 3C is a bar graph depicting the results of a luciferase reporter assay conducted in HeLa cells co-transfected with BRCA1 3'UTR-luciferase reporter, wildtype (WT, striped) or mutant (M, grey) with control mimic (miR-scr, black) or miR-182 mimic (striped and grey). Firefly luciferase activity of the reporter was normalized to an internal *Renilla* luciferase control. miR-182 significantly (*p<0.001) suppressed luciferase activity of BRCA1-WT reporter but mutation in the miR-182 recognition sites in BRCA1-M rescued this suppression (*p<0.001). Mean±SD, n=3 independent experiments. Above the bar graph is a stick diagram showing the location of the four miR-182 binding sites in the 3'UTR of BRCA1.
FIG. 3D is a photograph of a Western blot of lysates from HL60 cells that were transiently transfected with expression vectors for miR-183, miR-96, miR-182 and control (miR-scr) probed with anti-BRCA1 antibodies. The indicated non-specific band served as a visual representation for a loading control.

U2OS-DR-GFP cells, with a single, stably integrated copy of the transgenic reporter DR-GFP were seeded ($0.35 \times 10^6$ cells/well) into the wells of a 6-well tissue culture plate, transfected with a control and an miR-182 expression construct. Cells were selected for 4 weeks with 100 µg/ml of puromycin. mir-182 overexpression was confirmed with qPCR (FIG. 3C). HR assay was done as described (Chowdhury et al., Mol. Cell, 31:33-46 (2008)). Briefly, $2\times10^5$ cells plated overnight in 24-well plates were transfected with 0.8 µg of I-SceI expression plasmid (pCBA Sce) using Lipofectamine 2000. 2 days later, GFP positive cells were assayed by FACScan flow cytometer.

Clonogenic Assay.

Hela cells ($0.35\times10^6$ cells/well), MDA-MB231 cells ($0.4\times10^6$ cells/well), 21NT cells ($0.5\times10^6$) were seeded overnight and transfected with 10 nM of miRNA mimics or antagomirs (Ambion, Austin, Tex.) using Lipofectamine 2000. In rescue experiments, miR-182 or control mimics were co-transfected with 1 µg/ml BRCA1 (pcDNA3.1 vector). After 2 days, 1000 cells in 4 ml DMEM media (10% FBS v/v) were seeded on 6 cm tissue culture dishes in four replicates and allowed to attach overnight before treatment. PARP inhibitors (4-amino-1,8-naphthalimide (Sigma, St. Louis, Mo.) or ABT-888 (ChemieTek, Indianapolis, Ind.) in DMSO) were added to the growth media at indicated concentrations. Irradiated cells as well as cells in the presence of PARP inhibitor were allowed to form colonies for 14 days. For evaluation, formed colonies were stained with crystal violet and surviving colonies containing >50 cells were counted. Plating efficiency was 30-50%.

Cell Cycle Analysis.

U2OS cells ($0.35\times10^6$ cells/well) were transfected with 10 nM control mimic or miR-182 mimic and, in rescue experiments, co-transfected with 1 µg of BRCA1 (lacking 3'UTR) expression construct using Lipofectamine 2000. After 2 days, cells were seeded into the wells of 12-well tissue culture plates, incubated overnight, irradiated (5 Gy) and released in nocadozole (200 ng/ml) containing media after 2 hours. The next day the cells were stained with primary Phospho-H3 (Ser10) antibodies 1:100 dilution (Upstate Biotechnology, Lake Placid, N.Y.) and FITC-labeled secondary antibodies 1:50 dilution (Santa Cruz Biotechnology, Santa Cruz, Calif.) and analyzed by flow cytometry.

MCF-7 cells were differentiated with 100 nM TPA. At day 0, 1, 2, and 3 cells were collected, fixed with 70% cold ethanol and stored at −20° C. Permeabilized cells were centrifuged, washed once with PBS, and incubated for 30 minutes in propidium iodide (PI)/RNase Staining Buffer (BD Pharmingen, San Diego, Calif.) at 25° C. before flow cytometric analysis.

miRNA Microarrays of Primary Breast Tumors and Treatment.

This study includes samples from a historical series of breast cancer patients (n=210) treated in Oxford, UK, between 1989 and 1992. Patients received surgery followed by adjuvant hormone therapy or no adjuvant treatment. Details of treatment of patients with ER negative tumors is as follows:

|                  | Had Chemotherapy | | |
| --- | --- | --- | --- |
| Had Radiotherapy | No | Yes | Total |
| No  | 11 | 5  | 16 |
| Yes | 40 | 28 | 68 |
| Total | 51 | 33 | 84 |

This series and the RNA extraction procedure has previously been described (Camps et al., Clin. Cancer Res., 14:1340-8 (2008); Gee et al., Nature, 455:E8-9; author reply E9 (2008) all of which are incorporated herein by reference in their entireties). miRNA expression was measured using the Illumina microRNA arrays version 1.0. The preparation and hybridization of the samples was done using the reagents and instructions supplied by the manufacturer. Briefly, 200 ng of total RNA was poly-adenylated and converted to biotinylated cDNA using standard procedures. The biotinylated cDNA was attached to a solid phased and hybridized with a pool of microRNA-specific oligonucleotides (MSO). Each single MSO was used to assay one miRNA in the panel. Universal PCR amplification was then performed, creating fluorescently labeled products identifiable by their unique MSO sequence. These products were hybridized on the Illumina microarray array. The address sequence from each MSO allowed the hybridization of specific miRNA products to specific locations on the BeadArray substrate. Hybridization signals were detected and quantified using an Illumina scanner and BeadStudio Software. Average signal values were background subtracted by using a local background subtraction method (BeadStudio). Expression was normalized using quantile normalization.

Illumina mRNA Arrays for Tumor Samples.

Illumina Human RefSeq-8 arrays (Illumina Inc., San Diego, Calif., USA) were used. RNA was amplified using an Ambion Illumina Amplification Kit (Catalog #I1755). 850 ng of amplified RNA product was hybridized to the Illumina Sentrix Beadchip 8×1 GAP REFSEQ2 using single chamber hybridization cartridges. Washing and staining were carried out as specified in the Illumina Whole Genome Expression Manual version 1. Beadchips were scanned using the Illumina BeadArray Reader, a confocal-type imaging system with 532 (cy3) nm laser illumination. Expression data was extracted using the Illumina proprietary software BeadStudio, using background subtraction, rescaling was used to eliminate negative values, and normalization was done in Bioconductor (R) using quantile normalization. Three BRCA1 probe sets were present on these arrays, namely GI_6552306-A, GI_6552322-I, GI_6552300-I, which interrogate the transcripts NM_007298, NM_007306, NM_007295 respectively.

Immunohistochemistry and Scoring of ER Negative Tumors.

Immunohistochemistry was carried out on tissue microarray (TMA) 069 assembled with tissue cores from 104 consecutive breast carcinomas patients undergoing surgery at the John Radcliffe Hospital, Oxford, UK. TMA 069 was prepared as previously described, with minor modifications (Van den Eynden et al., Breast Cancer Res. Treat., 85:13-22 (2004)). Research on the tissue samples used in this study was approved by the local research ethics committee. Briefly, the microarray slide was de-waxed, rehydrated, washed, and subjected to microwave retrieval in a Citrate buffer (pH 6.0) for 2 minutes. Anti-BRCA1 antibody (epitope 1-304, Oncogene: MS110) diluted 1:100 was used, and immunoexpression was detected using a peroxidase-labeled streptavidin-biotin complex. Hematoxylin counterstaining was performed on the histology slide. Anti-BRCA1 MS110 antibody has been extensively validated for immunohistochemistry in previous publications (Wilson et al., Nat. Genet., 21:236-40 (1999); Elstrodt et al., Cancer Res., 66:41-5 (2006) both of which are incorporated herein in their entireties). The controls used to validate our immunohistochemistry method were paraffin embedded MCF7 cell pellets, paraffin sections of normal breast, sections of breast cancer patients obtained from the Cellular Pathology Department at the John Radcliffe Hospital in Oxford, UK, and patient tumor samples known to have mutated BRCA1 genes. Scoring of tumor cells in each cancer core was performed using the percentage of nuclear positive tumor cells (range 0-100%) and the intensity of the brown staining in the nucleus of cancer cells. Staining intensity was scored as 1+ for pale staining, 2+ for moderate staining and 3+ for dark staining and the % cells was categorized into 5 groups: 0%, 1-10%, 11-50%, 51-80% and 81-100%. An overall score was calculated for each core by multiplying the % cells and the intensity. A similar strategy has been used for scoring in breast cancer tissue (Douglas-Jones et al., J. Clin. Pathol., 54:951-5 (2001) which is incorporated herein in its entirety). As the statistical distribution of events was not even between scores, we considered the following scoring groups for further testing:

BRCA1 score=0. No staining in the nucleus: BRCA not expressed or mutated.

Low BRCA1: score≤1-3 (A score of 3 is equivalent to scenarios such as intensity of 1 in 51-80% of cells, or to intensity of 3 only in 1-10% of cells)

High BRCA1: score≥4 (The minimum score (=4) includes scenarios such as intensity of 1 in 81-100% of cells, or intensity of 2 in 11%-50% cells).

Statistical Analysis.

Association analyses, unless otherwise specified, were done using a non-parametric association test. Spearman correlation was used for continuous variables and the Wilcox test was used for a categorical variable versus a continuous variable. The Log-Rank test was used for univariate survival analysis and Cox survival analysis was used for multivariate analysis. Backward likelihood was used as a variable selection criterion. Distant-relapse free survival (DRFS) and relapse-free survival (RFS) were calculated as described by the STEEP criteria (Hudis et al., J. Clin. Oncol., 25:2127-32 (2007)).

Example 2

Identification of miRNAs that Regulate the DNA Damage Response

It was hypothesized that in post-mitotic blood cells DNA damage induces apoptosis and miRNAs attenuate the DSB repair machinery promoting cell death. Conversely, it was postulated that upon irradiation of proliferating progenitor cells, these miRNAs are down modulated resulting in an increased production of DNA repair proteins and upregulation of the DNA damage response.

In order to identify the differentiation-induced miRNAs that play a role in the DNA damage response, proliferating progenitor K562 cells and post-mitotic differentiated K562 cells (cells were treated with 12-O-tetradecanoylphorbol-13-acetate (TPA) to produce terminally differentiated megakaryocytes) were exposed to gamma irradiation and the expression of miRNAs was studied by microarray analysis. This experiment focused on the IR-response of 50 miRNAs that have previously been shown to be upregulated in multiple blood lineages (Lal et al., Nat. Struct. Mol. Biol., 16:492-8 (2009)).

Figure 1:
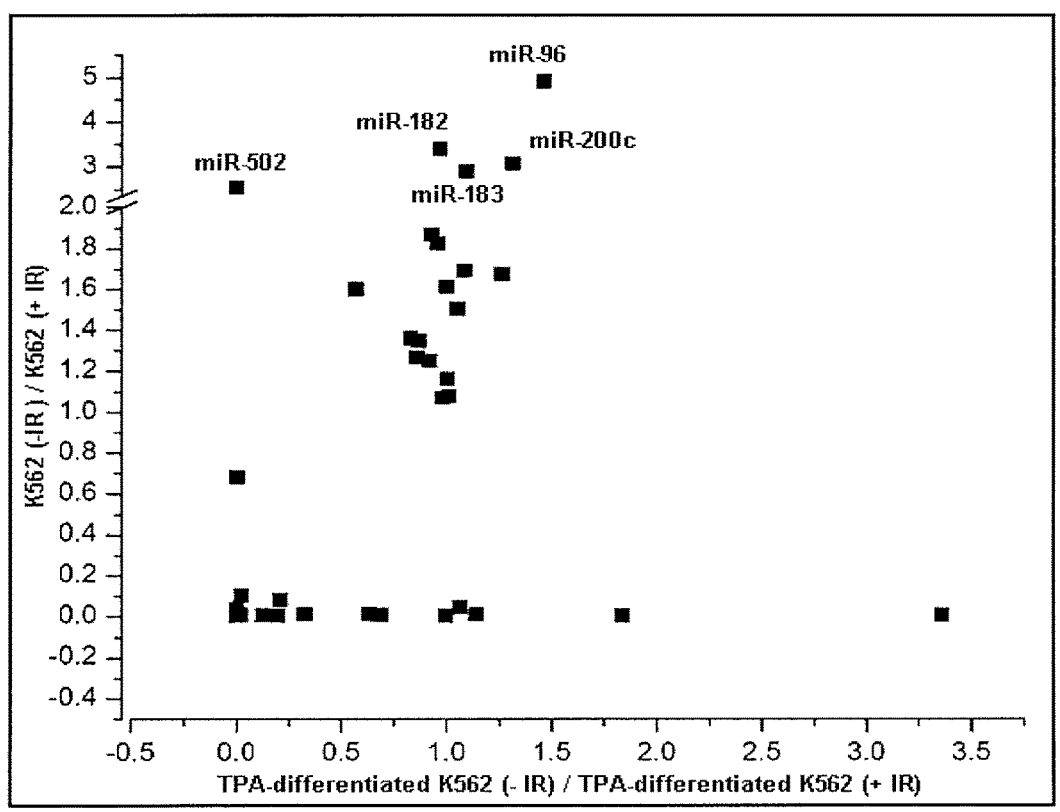
FIG. 1 is a 2-dimensional scatter plot showing the IR-induced change in expression of 50 miRNAs that are significantly upregulated in multiple lineages during in vitro hematopoietic differentiation. K562 cells and 12-O-tetradecanoylphorbol-13-acetate (TPA)-treated K562 cells (megakaryocytes) were exposed to 2 Gy of γ-radiation and total RNA harvested after 1 hr. The indicated miRNAs are significantly (<2-fold) downregulated by IR in K562 cells but remain unchanged in the post-mitotic TPA treated cells.
Figure 4:
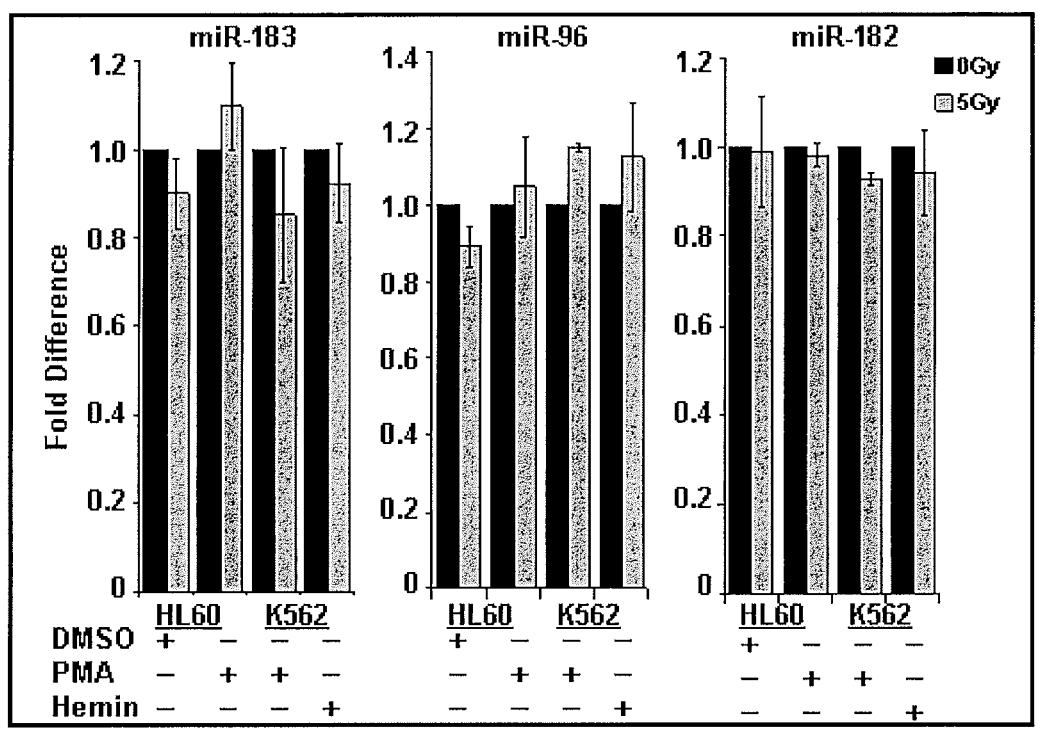
FIG. 4 is a bar graph depicting the response of miR-183 cluster to ionizing γ-radiation (IR) in differentiated HL60 and K562 cells. Terminally differentiated HL60 and K562 cells were exposed to 5 Gy IR, and RNA isolated 30 min after exposure. Expression of miR-183, miR-96, and miR-182 was analyzed with qRT-PCR and normalized to RNU6B. Mean, ±SD, n=3-6 independent experiment, p>0.3, is shown.

Following exposure to IR, only 5 miRNAs were down-regulated >2-fold in the proliferating K562 cells but not in the post-mitotic cells (FIG. 1). The 3 miRNAs in this set, miR-96, miR-183 and miR-182, are encoded in a ~5-kb gene segment. They are processed from the same polycistronic transcript on human chromosome 7q32.2 with conservation of synteny on mouse chromosome 6qA3 (FIG. 2). These miRNAs (termed miRNA cluster-183) have a sensory role (Lewis et al., Nat. Genet., 41:614-8 (2009); Mencia et al., Nat. Genet., 41:609-13 (2009) and are expressed at high levels in mouse retina and sensory hair cells of the ear (Xu et al., J. Biol. Chem., 282:25053-66 (2007); Pierce et al., Evol. Dev., 10:106-13 (2008); Friedman et al., Proc. Natl. Acad. Sci. USA 106:7915-20 (2009); Jin et al., Mol. Vis. 15:523-33 (2009)). miRNA cluster-183 is aberrantly expressed in a variety of tumors (Segura et al., Proc. Natl. Acad. Sci. USA, 106:1814-9 (2009); Bandres et al., Mol. Cancer. 5:29 (2006); Zhang et al., Proc. Natl. Acad. Sci. USA, 103:9136-41 (2006); Hanke et al., Urol. Oncol., (Apr. 16, 2009); Gaur et al., Cancer Res., 67:2456-68 (2007)). and is potentially useful for tumor classification (Gaur et al., Cancer Res., 67:2456-68 (2007)). The microarray results were verified by qRT-PCR. miR-183, miR-96 and miR-182 were significantly up-regulated during terminal differentiation of HL60 and K562, (FIG. 3A). There was no significant change in expression of miRNA cluster-183 in differentiated cells exposed to IR (FIG. 4). This observation is consistent with the hypothesis that the miRNA cluster-183 contributes to DNA damage-induced cell death in post-mitotic cells (Lal et al., Nat. Struct. Mol. Biol., 16:492-8 (2009)). However there was a sharp decrease in expression of miR-96, miR-183 and miR-182 in undifferentiated HL60 cells (FIG. 3B) within 30 min of IR exposure. Importantly, the expression levels diminished in an IR dosage-dependent manner. The rapid and dramatic change in expression of these miRNAs in response to IR suggests a direct involvement in the DNA damage response.

Example 3

BRCA 1 is a Potential Target of miR-182

It was postulated that miRNA cluster-183 was rapidly downregulated in response to IR in dividing cells to allow increased production of DNA repair factors and facilitate the DNA damage response. In order to identify DNA repair factors targeted by these miRNAs a computational approach was adopted. Several of the available prediction algorithms (such as TargetScan and Pictar) are largely based on evolutionary conservation of target sites of miRNAs across species (Bartel, Cell, 136:215-33 (2009); Sethupathy et al., Nat.

Figure 5:
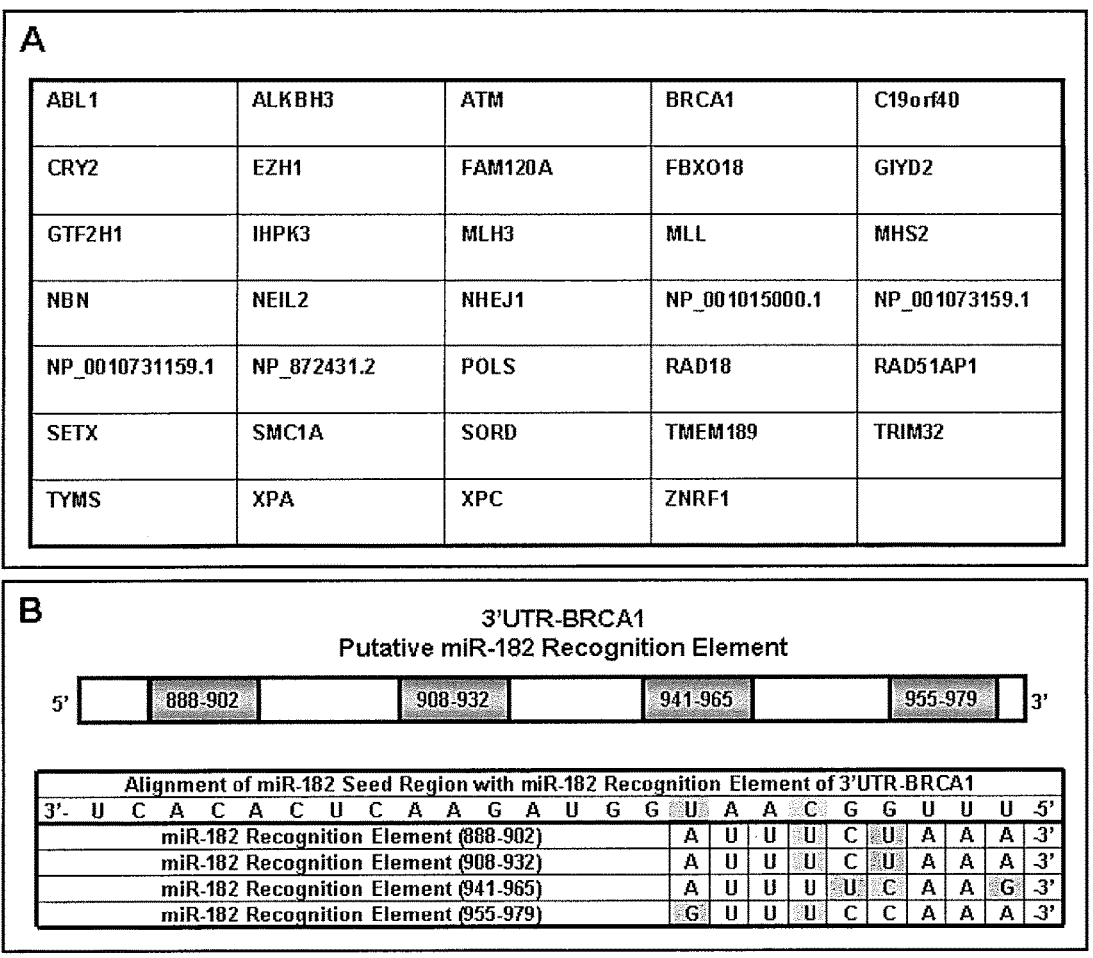
FIG. 5A is a chart listing the predicted DNA repair protein targets of miR-182 predicted by RNA22 (cbcsrv.watson.ibm.com/rna22.html).
FIG. 5B is a schematic diagram showing the predicted miR-182 binding sites in the 3'UTR of BRCA1 mRNA. Below this diagram is an alignment of the miR-182 sequence (SEQ ID NO:1) with the four predicted miR-182 binding sites (MRE) in the BRCA1 3'UTR including the target sites at positions 888-902 (SEQ ID NO:44); 908-932 (SEQ ID NO:44); 941-965 (SEQ ID NO:45); and 955-979 (SEQ ID NO:46). The MRE (908-932) was confirmed by RNA22, RNAhybrid and PITA. The other 3 MREs were predicted by PITA (genie.weizmann.ac.il/pubs/mir07/mir07_prediction.html).

Methods, 3:881-6 (2006)). However several critical DSB repair factors (such as MDC1, 53BP1, DNA-PK, BRCA1 and BRCA2) are not found in lower eukaryotes, potentially making these algorithms less effective in identifying DNA repair targets. RNA22 which is distinct from other methods in that it obviates the use of a cross-species sequence conservation filter allows the discovery of miRNA binding sites that may not be present in closely related species was used (cbcsrv.watson.ibm.com/rna22.html) (Miranda et al., Cell, 126:1203-17 (2006)). One limitation of this method is that it predicts hundreds or even thousands of potential targets for each miRNA, making it difficult to identify the most important targets. The problem was further compounded by the fact that 3 miRNAs had been identified, and there was a cumulative list of targets. Thus, miR-182, which was predicted to target BRCA1 was chosen as the focus of the experiments.

miR-182 is predicted to target several DSB repair proteins (FIG. 5A), which include BRCA1, NHEJ1/XLF etc. The BRCA1 3'UTR is (~1400 nt) long and has 4 potential miR-182 miRNA recognition elements (MRE) (FIG. 3C, upper panel and FIG. 5B). However, bioinformatic algorithms have a high margin of error and the majority of predicted genes may not be real targets (Sethupathy et al., Nat. Methods, 3, 881-6 (2006)).

Example 4

BRCA1 is Regulated by miR-182

To verify that BRCA1 is regulated by miR-182, the effect of miR-182 on expression of a luciferase construct with the BRCA1 3'UTR in HeLa cells was tested. Luciferase activity was reduced more than 2-fold by miR-182 expression in cells transfected with wildtype BRCA1-reporter. Mutation of the predicted MREs significantly reduced the effect of miR-182 on luciferase expression (FIG. 3C).

Next, BRCA1 expression levels were examined after ectopic overexpression of miR-182 and a significant decrease in BRCA1 protein (FIG. 3D) and a moderate decrease in BRCA1 mRNA was observed (data not shown). Importantly, overexpression of miR-183 and miR-96, which are co-expressed with miR-182, did not affect BRCA1 protein levels.

Example 5 miR-182/AGO1 Complex Associates Selectively with the BRCA1 Transcript

Figure 7:
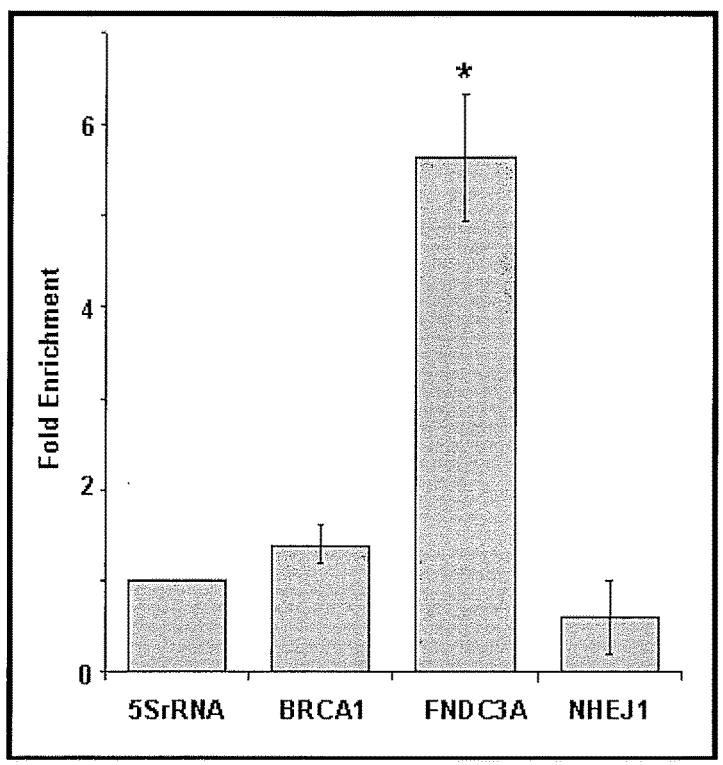
FIG. 7 is a bar graph showing the fold enrichment of several transcripts with the miR-17/AGO complex. MDA-MB231 cells were co-transfected with expression vectors encoding HA-tagged AGO1 and miR-17. The immunoprecipitated RNA was analyzed by qRT-PCR using gene-specific primers and normalized to 5S rRNA. FNDC3A has been reported to co-immunoprecipitate with a mir-17/AGO complex and served as positive control. FNDC3A was significantly enriched (*p<0.009), whereas BRCA1 and NHEJ1 were not (p>0.62). Mean±SD, n=3 independent experiments.

BRCA1 is an integral component of the cellular DNA damage response (Kim et al., Mol. Cell, 25:457-61 (2008); Boulton, Biochem. Soc. Trans. 34:633-45 (2006)). However, its expression specifically impacts breast tumor development and therapy Mullan et al., Biochim. Biophys. Acta, 1766:205-16 (2006); Narod et al., Nat. Rev. Cancer, 4:665-76 (2004); Palacios et al., Pathobiology, 75:85-94 (2008)). Therefore this experiment focused on characterizing the physiological relevance of miR-182-mediated regulation of BRCA1 in breast cancer cells. Computational predictions of miRNA targets are typically made on a genome wide scale irrespective of tissue-specific miRNA/mRNA interactions. To confirm that miR-182 targets the BRCA1 transcript in breast cancer cells a recently described biochemical approach (Hendrickson et al., PLoS ONE, 3:e2126 (2008); Easow et al., Rna, 13:1198-204 (2007)) was adapted. miR-NAs target their corresponding mRNAs in association with a protein complex that includes the Argonaute proteins, AGO1 and AGO2. This interaction allows for the identification of miRNA-target interactions that occur in vivo. Immunoprecipitation (IP) of a hemagglutinin (HA)-tagged AGO1 can recover miRNA/mRNA complexes. In cells that overexpress a specific miRNA, IP of HA-AGO1 selectively enriches for the overexpressed miRNA and its corresponding target mRNAs. Using this strategy in the breast cancer line MDA-MB231 it was found that the miR-182/AGO1 complex associates selectively with the BRCA1 transcript (FIG. 6A) at levels comparable with a validated miR-182 target, FOXO3 mRNA (Segura et al., Proc. Natl. Acad. Sci. USA, 106:1814-9 (2009)). Levels of BRCA1 mRNA were significantly higher than control transcripts (5S rRNA and GAPDH mRNA) and other predicted targets (NHEJ1 mRNA). Interestingly, another miRNA, miR-17, predicted to target BRCA1 (Shen et al., Int. J. Cancer, 124:1178-82 (2009)) did not associate with BRCA1 transcript in this assay system (FIG. 7). It was also confirmed that overexpression of miR-182 sharply reduced BRCA1 protein levels in these cells (FIG. 6B).

Example 6

BRCA1 is a Physiologically Relevant Target of miR-182 in Breast Cancer Cells

Figure 8:
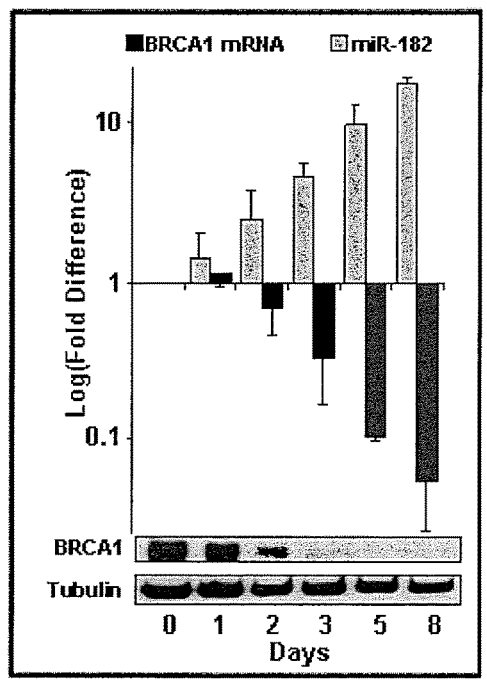
FIG. 8 is a bar graph showing the log fold difference in the kinetics of miR-182 and BRCA1 mRNA expression (upper panel) in DMSO-treated HL60 cells compared with a photograph of a western blot depicting BRCA1 and tubulin protein expression (lower panel). miR-182 and BRCA1 transcripts were quantified by qRT-PCR and normalized to RNU6B and 5S rRNA, respectively. Mean±SD, n=4 independent experiments, BRCA1 mRNA p<0.00078, miR-182 p<0.0021.
Figure 9:
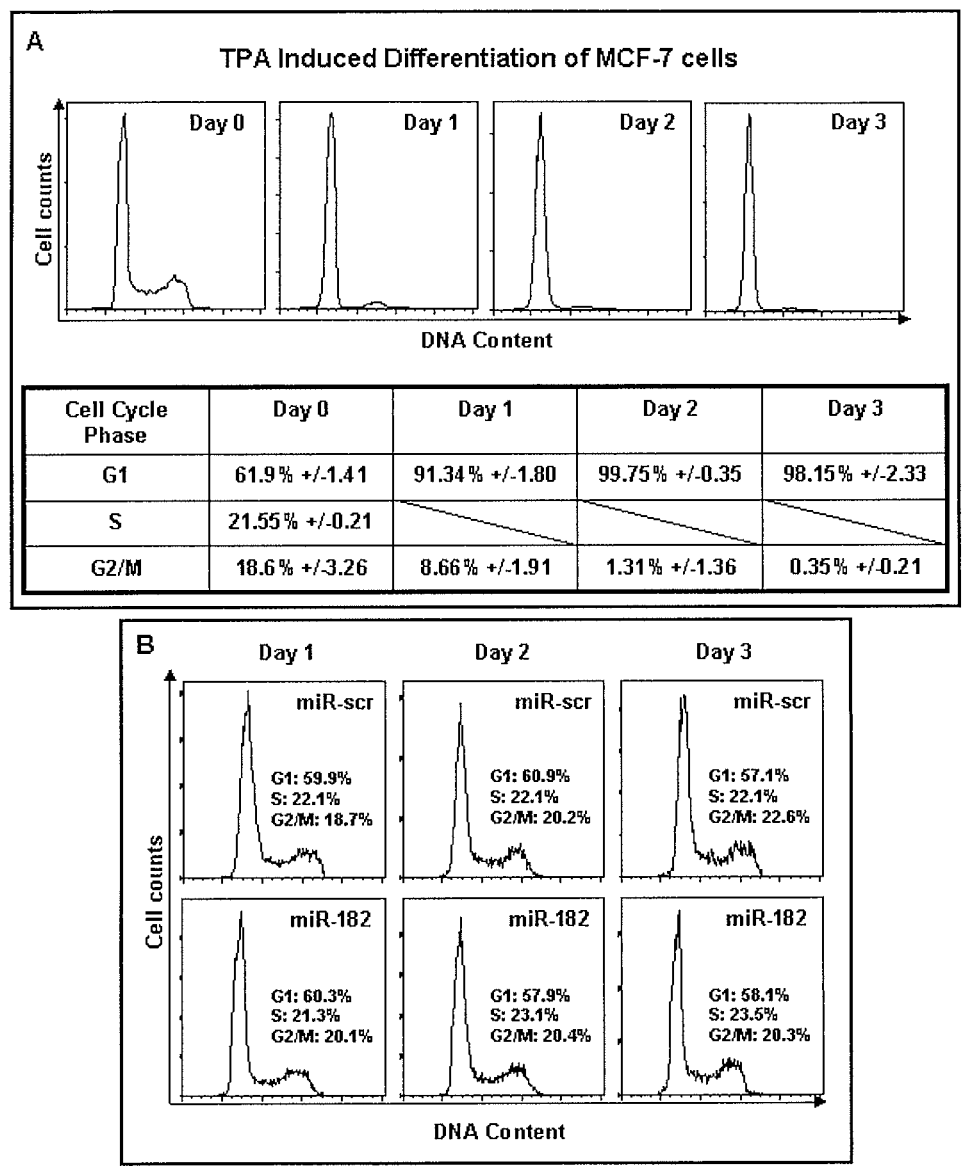
FIG. 9A is a series of one dimensional fluorescent flow cytometry (FFC) histograms and tables that show the effect of TPA-treatment on the cell cycle in MCF7 cells. MCF7 cells were treated with 100 nM TPA and collected at day 0, 1, 2 and 3 as indicated. The cells were fixed with 70% ethanol, stained with propidium iodide (PI) and analyzed by flow cytometry. Representative flow cytometry images are shown in the upper panel, and the results from 3 independent experiments are represented in the table.
FIG. 9B is a series of one dimensional FFC histograms and tables to show the effect of TPA-treatment on the cell cycle in MCF7 cells that were transfected with either control mimic (miR-scr) or miR-182 mimic (miR-182) and analyzed as described in FIG. 9A.

The physiological relevance of the miR-182/AGO1 interaction with BRCA1 was further established by evaluating the endogenous expression pattern of miR-182 and BRCA1. TPA treatment of blood cells arrest cell division and induces expression of miR-182 (FIG. 3A) with a corresponding decrease in BRCA1 levels (FIG. 8). It has been reported that TPA treatment of breast cancer lines leads to a post-mitotic state (Cunliffe et al., Cancer Res., 63:7158-66 (2003)), and this result was confirmed (FIG. 9). If miR-182 does regulate BRCA1 levels, then the prediction would be that BRCA1 levels diminish in parallel with increasing expression of miR-182. MCF7 cells were treated with TPA and the expression levels of miR-182 and BRCA1 were monitored over 3 days. Consistent with this prediction, a striking inverse correlation of BRCA1 protein levels with miR-182 expression was observed (FIG. 6C). These results suggest that miR-182, possibly in combination with other factors, leads to diminished BRCA1 levels in post-mitotic cells.

Like for blood cells, upon gamma irradiation treatment, there was rapid and dosage-dependent decrease of miR-182 expression in proliferating MCF7 cells, but not post-mitotic MCF7 cells (FIG. 6D). The relative decrease in miR-182 level with IR exposure in MCF7 cells is comparable to the level seen in primary human mammary epithelial cells (HMECs, FIG. 6E).

Together these results strongly suggest that BRCA1 is a physiologically relevant target of miR-182 in breast cancer cells.

Example 7

Expression of miR-182 and BRCA1 in Breast Cancer Cell Lines

Based on molecular profiling of tumors, breast cancer types have been divided into those with high expression of the ER gene (luminal) and those that do not express ER (basal) (Perou et al., Nature, 406:747-52 (2000)). ER-negative status is an intrinsic feature of BRCA1-related breast cancer (Atchley et al., J. Clin. Oncol., 26:4282-8 (2008); Foulkes et al., Clin. Cancer Res., 10:2029-34 (2004)).

Figure 11:
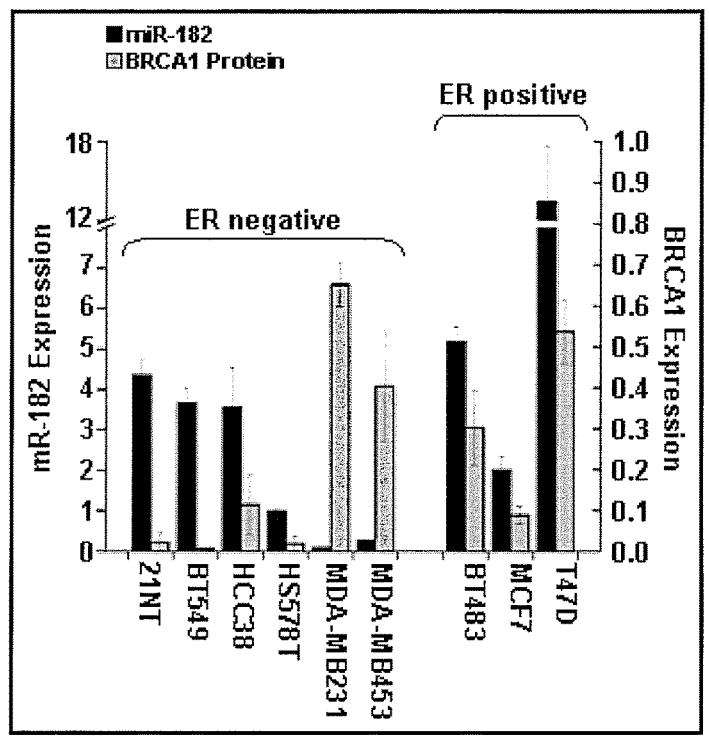
FIG. 11 is a bar graph showing that miR-182 expression inversely correlates with BRCA1 protein in ER-negative breast tumor cells. Relative BRCA1 expression was quantified by densitometry using tubulin as control and normalized to expression in HMEC.

BRCA1 protein and miR-182 expression were investigated in a panel of breast cancer lines derived from ER positive and negative tumors (FIG. 10A). Consistent with clinical data, the basal-like ER-negative cell lines 21NT, BT549, HS578T and HCC38 had relatively low levels of BRCA1 protein (Neve et al., *Cancer Cell*, 10:515-27 (2006)). No significant correlation of BRCA1 and miR-182 was found in ER-positive tumor cells; however, in the ER-negative cell lines there was a striking inverse correlation of BRCA1 protein and miR-182 expression (FIG. 10A, graphically represented in FIG. 11).

Example 8

Figure 12:
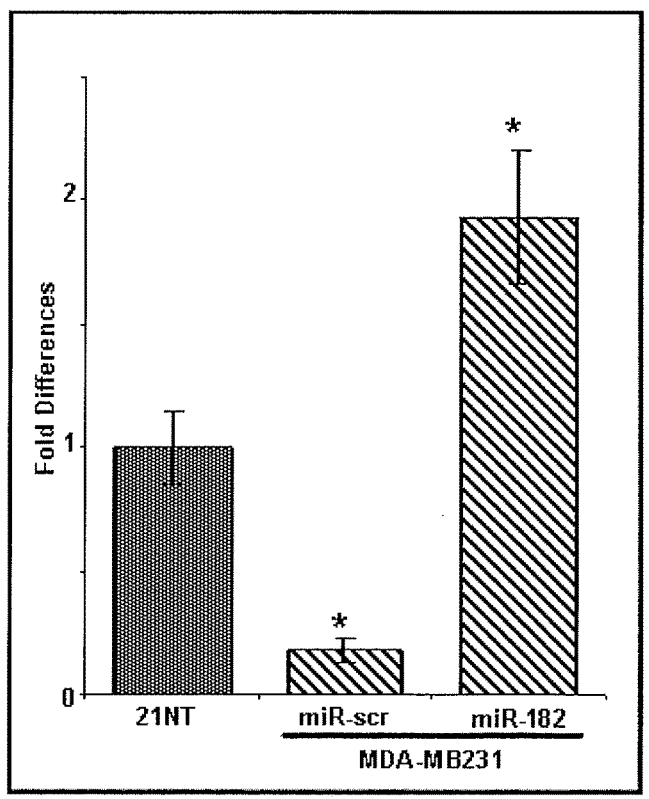
FIG. 12 is a bar graph showing the levels of miR-182 incorporated in the AGO-complex in MDA-MB231 cells via transfection of miR-182 mimic are comparable to levels of miR-182/AGO complex in 21NT cells. MDA-MB231 cells were co-transfected with expression vector for HA-tagged AGO1 and miR-182 mimic or control mimic. In parallel, 21NT cells were transfected with HA-tagged AGO1 and control mimic. The immunoprecipitated RNA from 21NT cells and MDA-MB231 cells were analyzed by qRT-PCR for miR-182 and normalized to RNU6B and mean±SD, n=3-6 independent experiments, *p<0.015.

Effect of miR-182-Mediated Downregulation of BRCA1 Expression on DNA Repair and the G2/M Checkpoint To determine whether miR-182-mediated BRCA1 downregulation in ER negative cell lines affects DNA repair, the persistence of DSBs after gamma irradiation was measured as an indicator of unrepaired damaged DNA, by single-cell gel electrophoresis (neutral comet assay, FIG. 10B).

miR-182 was overexpressed in MDA-MB231 cells (low endogenous miR-182, high BRCA1 protein) and miR-182 expression was reduced in 21NT cells (high endogenous miR-182, low BRCA1 protein). The BRCA1 levels in these cells and their DNA repair capacity were assessed. MDA-MB231 cells with ectopic overexpression of miR-182 had lower levels of BRCA1 protein and significantly higher residual DNA damage relative to control cells (FIG. 10B, left panel). Importantly, it was determined that the amount of miR-182 mimic introduced in MDA-MB231 cells, and incorporated in the AGO1 complex, was within a physiologically relevant range (FIG. 12). Conversely, 21NT cells transfected with miR-182 antisense oligonucleotides (termed antagomirs, ASO) had higher levels of BRCA1 protein and significantly lower amounts of DNA breaks (FIG. 10B, right panel).

Figure 13:
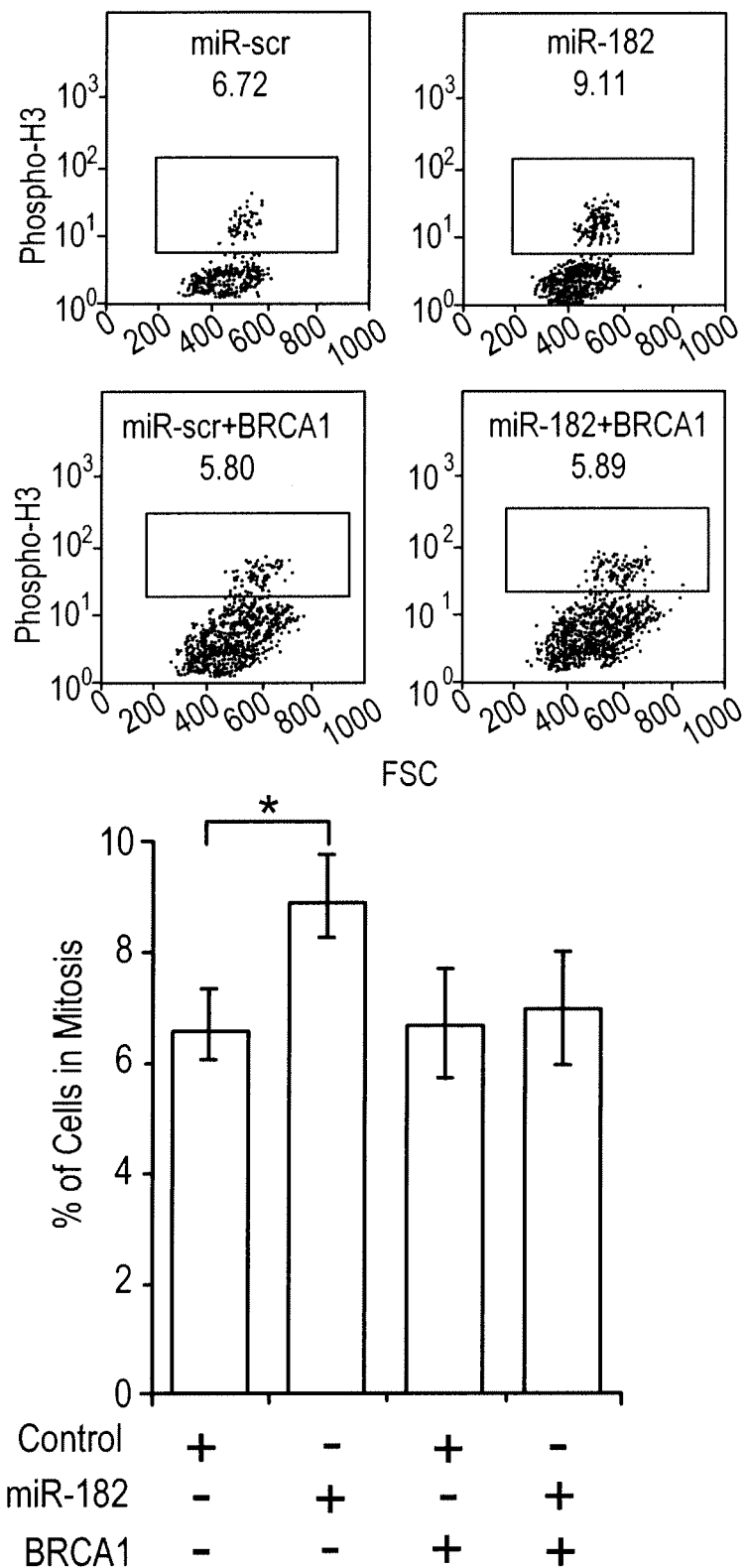
FIG. 13 is a series of two dimensional FFC histograms (upper panel) and a bar graph (lower panel) that show that miR-182-mediated down regulation of BRCA1 impacts the G2/M checkpoint. U2OS cells were transfected with control mimic alone, miR-182 mimic alone, or control mimic or miR-182 mimic plus BRCA1 lacking the 3'UTR. After 2 days these cells were exposed to ionizing γ-radiation (5 Gy) and supplemented with nocodazole (100 ng/ul for 24 hours). Percentages of cells arrested in mitosis were assessed with anti-phospho-S10-Histone H3 (P-H3) antibody and two dimensional FFC quantitation. The effect of miR-182 overexpression on mitosis was negated by co-transfection of BRCA1 lacking the 3'UTR. Representative two dimensional FFC histograms are shown in the upper panel, and the mean±SD, n=3 independent experiments, *p<0.012, is summarized in column plot in the lower panel.

BRCA1-deficient cells have an impaired G2/M checkpoint with more cells entering mitosis after IR (Yarden et al., *Nat. Genet.*, 30:285-9 (2002); Xu et al., *Mol. Cell. Biol.*, 21:3445-50 (2001)). miR-182 overexpression was found to affect the G2/M checkpoint with a significant increase in mitotic cells post-DNA damage (FIG. 13). Furthermore, the effect of miR-182 on the G2/M checkpoint was rescued by expression of miR-182-insensitive BRCA1 transcripts (FIG. 13).

Example 9 miR-182-Mediated Downregulation of BRCA1 Affects the Radiation Response of Breast Cancer Cells To determine the therapeutic impact of miR-182-mediated regulation of BRCA1 in breast cancer, miR-182 was overexpressed in MDA-MB231 cells and miR-182 expression in 21NT cells was reduced and the sensitivity of these cells to IR was assessed. Consistent with the DNA repair assays and G2/M checkpoint analysis described in Example 8, MDA-MB231 cells overexpressing miR-182 were significantly more sensitive to different doses of IR (FIG. 10C, left panel).

To determine whether the enhanced radiosensitivity of miR-182-overexpressing cells was mediated by BRCA1, MDA-MB231 cells were co-transfected with miR-182 and a miR-182-insensitive BRCA1 expression plasmid that lacks the BRCA1 3'UTR. Significantly, the effect of miR-182 on gamma irradiation sensitivity was fully rescued by overexpressing miR-182-insensitive BRCA1. Furthermore, antagonizing miR-182 expression in 21NT by miR-182-(ASO) induced significant radio-resistance in these cells (FIG. 10C, right panel).

Together these results strongly suggest that miR-182 mediated downregulation of BRCA1 significantly impacts the radiation response of breast cancer cells.

Example 10

Effect of miR-182 Mediated Downregulation of BRCA1 on HR-Mediated DSB Repair

Figure 14:
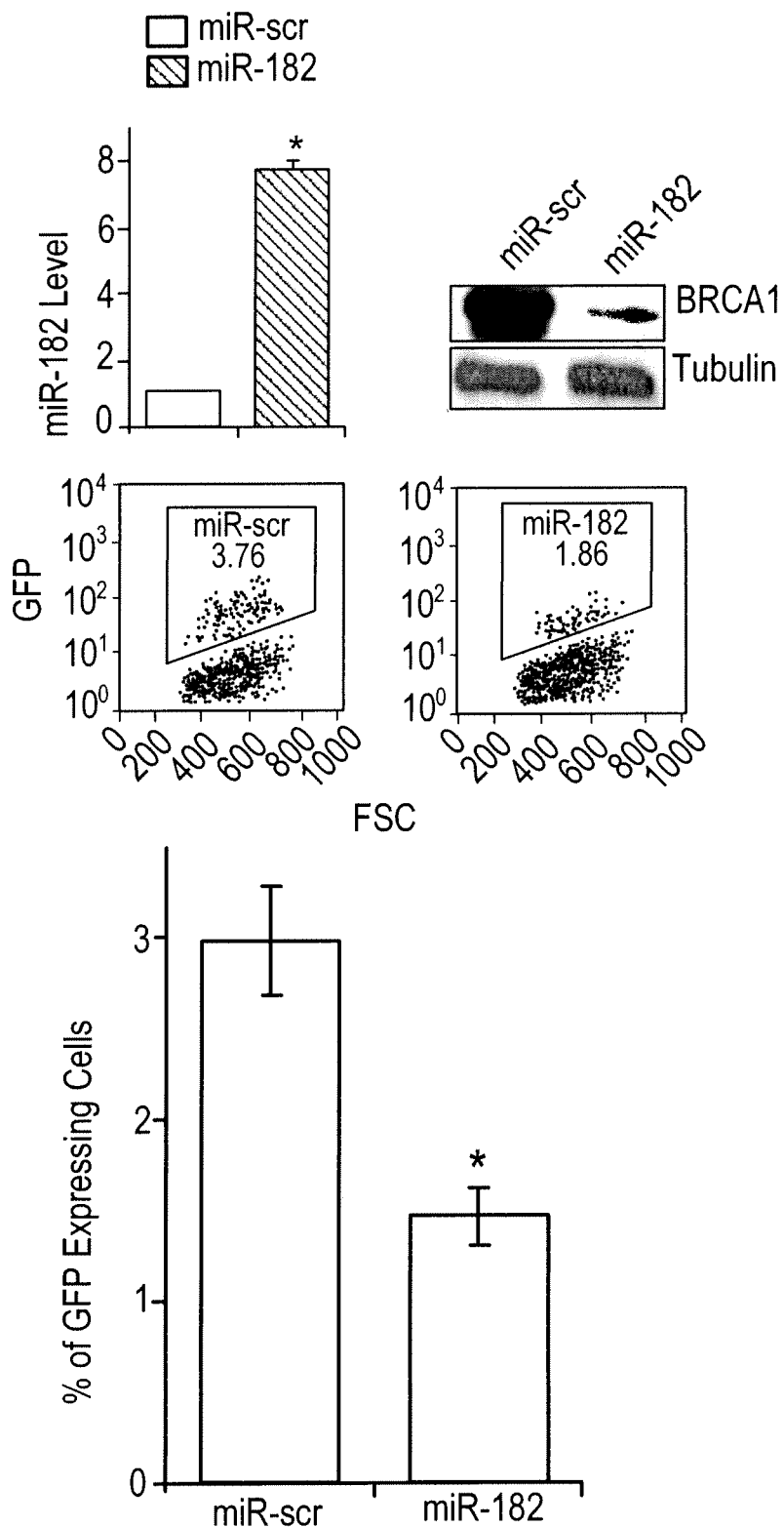
FIG. 14 is a representation of experiments showing that overexpression of miR-182 impedes homologous recombination-mediated repair (HR) of DSBs. U2OS cells carrying the recombination substrate (DR-GFP) were stably transfected with expression vectors for miR-182 or scrambled control. I-SceI expression plasmid was transiently transfected at day 4 and the GFP positive cells analyzed 48 hours later by FFC. miR-182 expression (upper panel) and representative two dimensional FFC profiles are shown (middle panel). HR repair was significantly (*p<0.002) impaired (lower panel). Mean±SD, n=3 independent experiments.

Although BRCA1 deficiency impairs HR-mediated DSB repair (Moynahan et al., *Mol. Cell*, 4:511-8 (1999)), it was not clear whether the miR-182-mediated reduction of BRCA1 levels would have any effect on HR. To address this issue, we assayed for HR-mediated restoration of a functional GFP gene by an I-SceI-induced DSB in the DR-GFP recombination substrate (Nakanishi et al., *Proc. Natl. Acad. Sci. USA*, 102:1110-5 (2005)). Consistent with the role of BRCA1 in HR (Moynahan et al., *Mol. Cell*, 4:511-8 (1999); San Filippo et al., *Ann. Rev. Biochem.*, 77:229-57 (2008)), cells overexpressing miR-182 had significantly reduced HR-efficiency (Supplemental FIG. 14).

Example 11

Effect of miR-182 Expression on Sensitivity of Cells to PARP1 Inhibitors

HR-deficiency of BRCA-mutation associated breast tumors selectively sensitizes them to PARP inhibitors (Farmer et al., *Nature*, 434:917-21 (2005); Bryant et al., *Nature*, 434:913-7 (2005)) which is an effective therapeutic strategy to eliminate these tumors (Fong et al., *N. Engl. J. Med.*, 361:123-34 (2009); Helleday et al., *Nat. Rev. Cancer*, 8:193-204 (2008); Lord et al., *Curr. Opin. Pharmacol.*, 8:363-9 (2008)).

Figure 15:
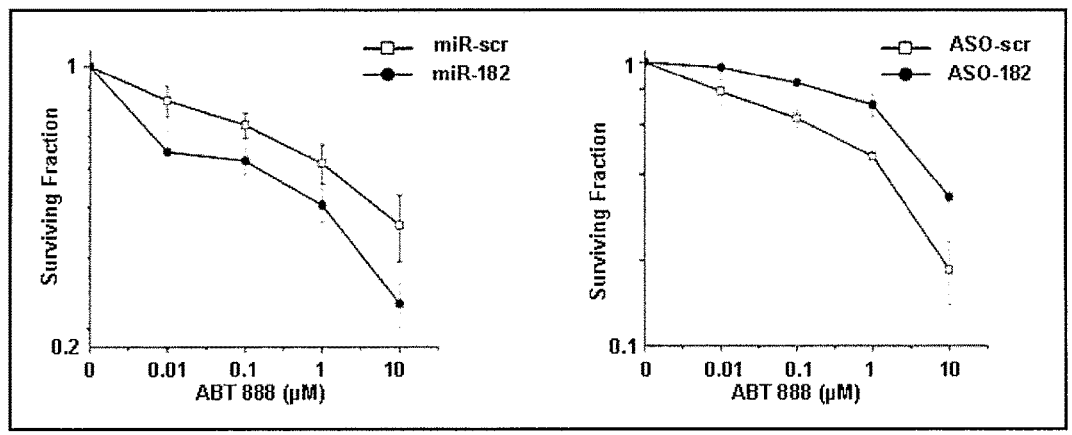
FIG. 15 is a set of line graphs that show that miR-182 impacts sensitivity to PARP1 inhibitor ABT-888 in breast tumor cells. MDA-MB231 cells (left panel) were transfected with either control mimic or 182 mimic. Conversely, 21NT cells (right panel) were transfected with either control ASO or 182 ASO. Cells were cultured for 14 days in media containing different concentrations of PARP1 inhibitor, ABT-888 and viability was assessed by clonogenic cell survival assay. Both plots represent mean±SD, (n=3) independent experiments, p<0.021 (left panel) and p<0.012 (right panel).

Based on the finding in Example 10 that cells overexpressing miR-182 had significantly reduced HR-efficiency, it was speculated that miR-182 expression may impact cellular sensitivity to PARP1 inhibitors. Overexpression of miR-182 was found to diminish BRCA1 levels and sensitize MDA-MB231 cells to PARP1 inhibition (FIG. 10D, left panel) using the PARP1 inhibitors, 4-Amino-1,8-naphthalimide (ANI) and ABT-888 (FIG. 15). As in FIG. 10C, this effect is reversed by expressing miR-182 insensitive BRCA1 transcripts. Conversely, reducing miR-182, enhanced BRCA1 expression and induced resistance to ANI (FIG. 10D, right panel) and ABT-888 (FIG. 15) in 21NT cells. Thus, modulation of miR-182 expression in ER-negative breast cancer lines has an impact on BRCA1 protein levels which correlates with sensitivity to PARP1 inhibition.

Figure 16:
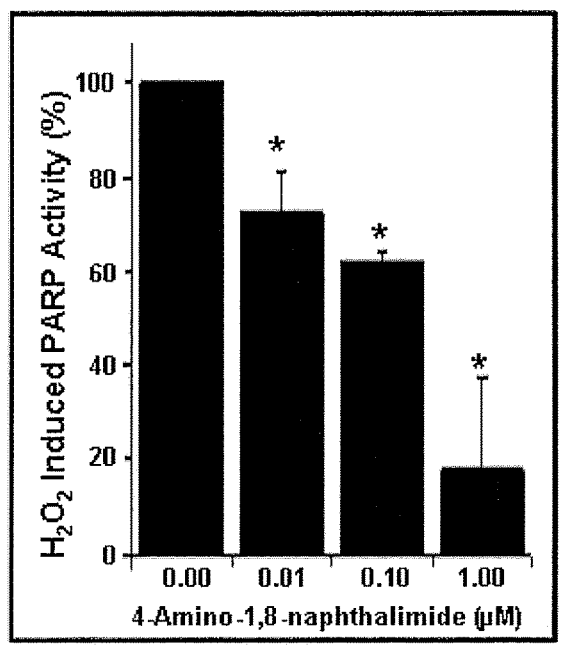
FIG. 16 is a bar graph that shows that the PARP inhibitor 4-Amino-1,8-naphthalimide inhibits PARP activity in MDA-MB231 cells. MDA-MB231 cells were treated with increasing concentrations of 4-Amino-1,8-naphthalimide for 10 minutes on ice prior to treatment with 100 µM $H_2O_2$ for 20 minutes on ice, in presence of 4-Amino-1,8-naphthalimide. The cells were then incubated for 10 min at 37° C. in $H_2O_2$-free medium with respective concentrations of 4-Amino-1,8-naphthalimide after which the cells were lysed and PARP activity measured using a universal PARP chemiluminescent assay kit (Trevigen) as per manufacturer's instructions. Mean±SD, n=3, *p<0.007.

That the impact of ANI was indeed due to PARP inhibition was confirmed by assaying PARP activity (FIG. 16). These results suggest that miR-182 is a novel mediator of the cellular response to PARP inhibitors. Importantly, the observation that the DNA repair deficient phenotype induced by miR-182 was largely rescued by miR-182 resistant BRCA1 transcripts (see Example 9), suggests that the key target of miR-182 in DNA repair is BRCA1.

Example 12 miR-182-Mediated Downregulation of BRCA1 Impacts Chemo- and Radiotherapy and Alters Patient Survival In order to determine whether the expression of miR-182 has any clinical relevance in breast cancer, miR-182 expression was investigated in primary breast tumors classified by ER expression. These experiments were performed to test the hypothesis that miR-182-mediated downregulation of BRCA1 may significantly impact chemo- and radiotherapy, and consequently alter patient survival.

Figure 17:
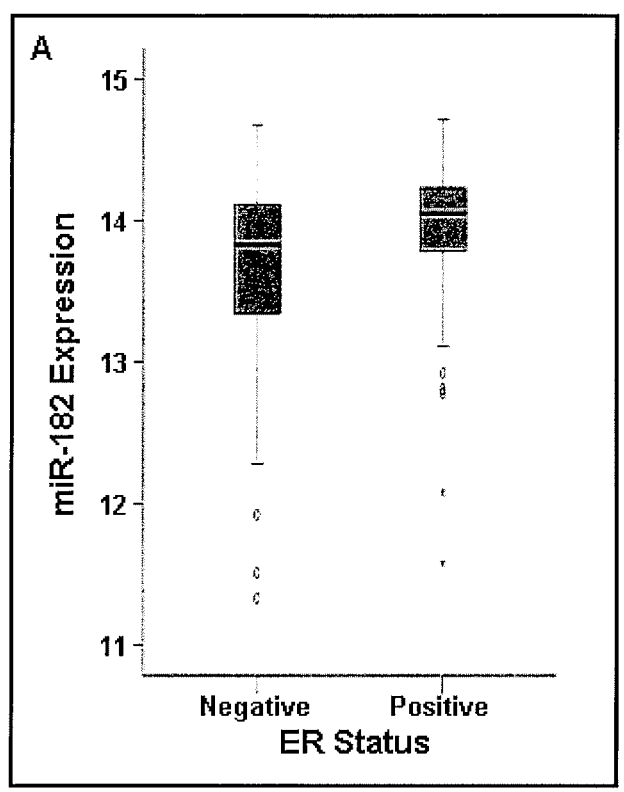
FIG. 17 is a box plot showing the levels of miR-182 expression in primary breast tumors. Analysis of miR-182 expression was carried out on primary breast tumors from 210 patients. These tumors were than grouped in estrogen receptor-positive (128 patients) and estrogen receptor-negative (82 patients) based on immunohistochemistry. The box plot represents the expression of miR-182 in primary breast cancer with respect to estrogen receptor status. Mann-Whitney U=3743.5, P=0.00046.
Figure 18:
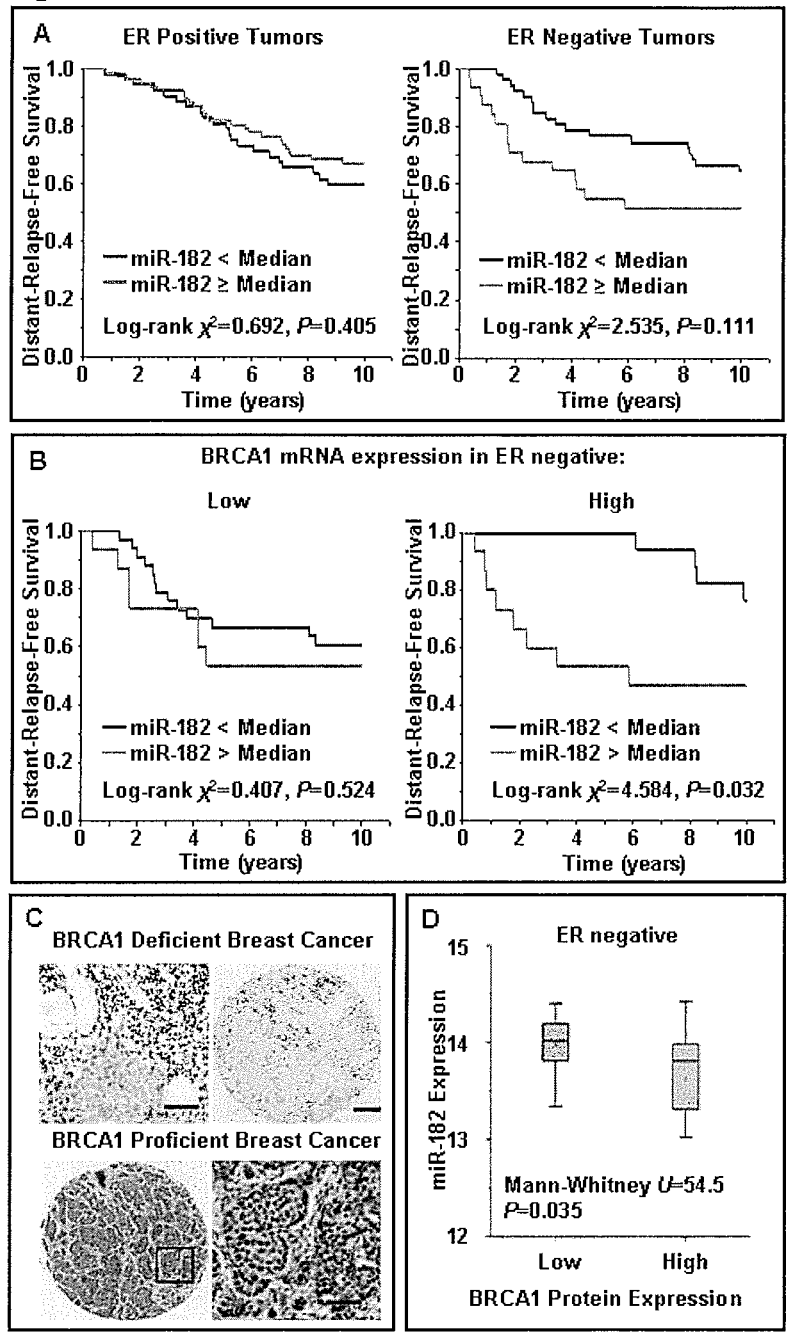
FIG. 18A provides Kaplan-Meier plots of miR-182 expression versus distant-relapse free survival (DRFS) in 210 patients with primary breast cancer. Tumors were divided by miR-182 expression median value. The plots are shown for 128 patients with ER-positive breast tumors (left panel) and 82 patients with ER-negative tumors (right panel).
FIG. 18B provides Kaplan-Meier plots of miR-182 expression versus distant-relapse free survival (DRFS) in ER-negative breast tumors expressing high levels of BRCA1 transcript. The plots are shown for 48 patients with low BRCA1 expression (left panel) and 32 patients with high BRCA1 expression (right panel).
FIG. 18C shows representative images of immunohistochemical staining for BRCA1 in breast cancer patient samples. The upper left panel depicts a negative control and shows BRCA1 staining conducted on tumor cells of a tissue section from a breast cancer patient with a documented BRCA1 mutation. The staining seen at the top of this panel corresponds to lymphocytes that stain positive for BRCA1 expression. Scale bar 100 µm. The upper right panel, corresponds to TMA069 breast cancer core that is negative for BRCA1 expression. Scale bar 200 µm. The bottom left panel depicts a TMA069 breast cancer core with strong BRCA1 intensity in the nuclei of 90% of tumor cells. The bottom right panel depicts the enlargement of the area marked by the square in the panel on the bottom left. Scale bar 50 µm.
FIG. 18D is a box plot showing that BRCA1 protein levels inversely correlate with miR-182 levels in ER-negative breast tumor tissue. Tumors were classified by high (17 samples) and low (12 samples) levels of BRCA1 protein.
Figure 19:
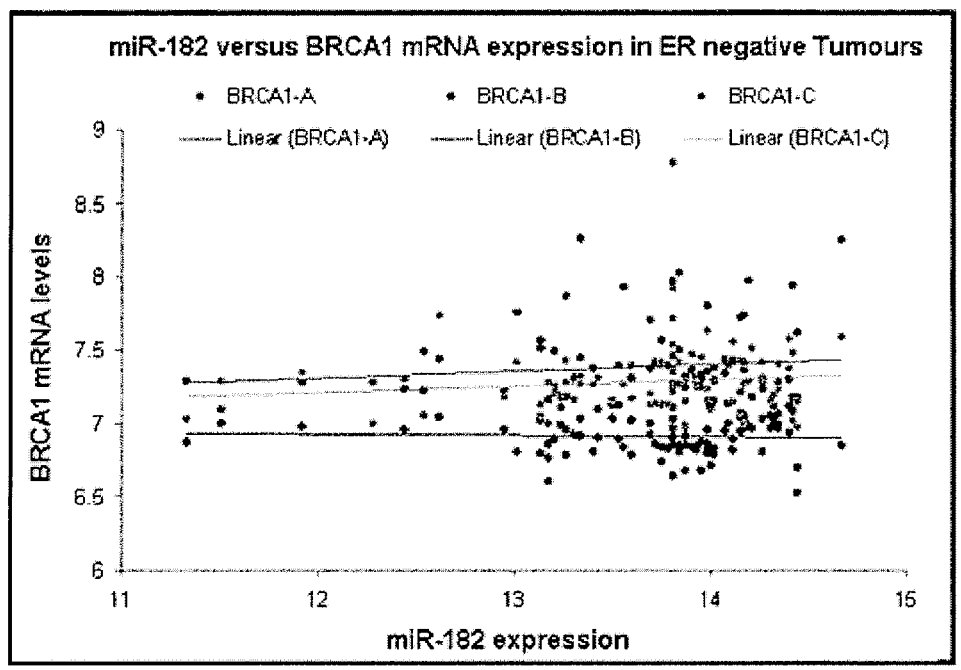
FIG. 19 shows linear fits for BRCA1 mRNA expression as a function of miR-182 expression in 82 ER-negative breast cancer samples using three BRCA1 mRNA probes.

Tumor samples from 210 patients with primary breast cancer, (clinical details described previously (Camps et al., *Clin. Cancer Res.*, 14:1340-8 (2008); Gee et al., *Nature*, 455:E8-9; author reply E9 (2008)), were analyzed for miR-182 expression. In an exploratory analysis, miR-182 levels in breast tumors was correlated with distant relapse-free survival (DRFS) over 10 years as described by the STEEP criteria (Hudis et al., *J. Clin. Oncol.*, 25:2127-32 (2007)). Although miR-182 was expressed at high levels (FIG. 17), there was no correlation of miR-182 expression levels with overall survival in the 128 patients with ER-positive breast tumors (FIG. 18A, left panel). In striking contrast, in the 82 patients with ER-negative tumors there was a clear trend to suggest an inverse correlation of miR-182 expression with survival. Tumors with low levels of miR-182 showed a better prognosis than tumors with high values of miR-182, although the difference did not reach statistical significance (FIG. 18A, right panel). In this population there was a wide variation of both miR-182 and BRCA1 transcript levels (FIG. 19). This variation would suggest that the final BRCA1 protein level may also vary considerably and cannot be predicted by its mRNA level.

Example 13

Inverse Correlation of miR-182 Expression with Survival in Patients that Express High Levels of BRCA1 Transcript It is noteworthy that miR-182 can significantly downregulate BRCA1 protein levels only in cells expressing BRCA1 mRNA. Therefore, it was hypothesized that miR-182 may impact breast cancer therapy in patients with tumors that have relatively high levels of BRCA1 transcript.

To test this prediction we classified the ER-negative tumors into 2 categories based on BRCA1 mRNA levels. In the absence of clinically defined cutoff point for BRCA1 transcript expression, we divided patients by median value of BRCA1 (FIG. 18B); three different transcripts corresponding to the three major BRCA1 transcripts were used with similar results. These two subsets were then further analyzed for miR-182 expression and DRFS over 10 years. There was a striking inverse correlation of miR-182 expression with survival only in patients that expressed high levels of BRCA1 transcript, and importantly, this difference was statistically significant (FIG. 18B).

As an alternative approach we used Bayesian clustering and identified two distinct groups of tumors expressing low and high levels of BRCA1 transcripts, respectively. In this case also there was a significant inverse correlation of miR-182 expression with survival in the high-BRCA1 cluster (Log-rank $\chi^2$=5.54, p=0.02) but not in the low-BRCA1 cluster (Log-rank $\chi^2$=0.91, p=0.34).

Figure 20:
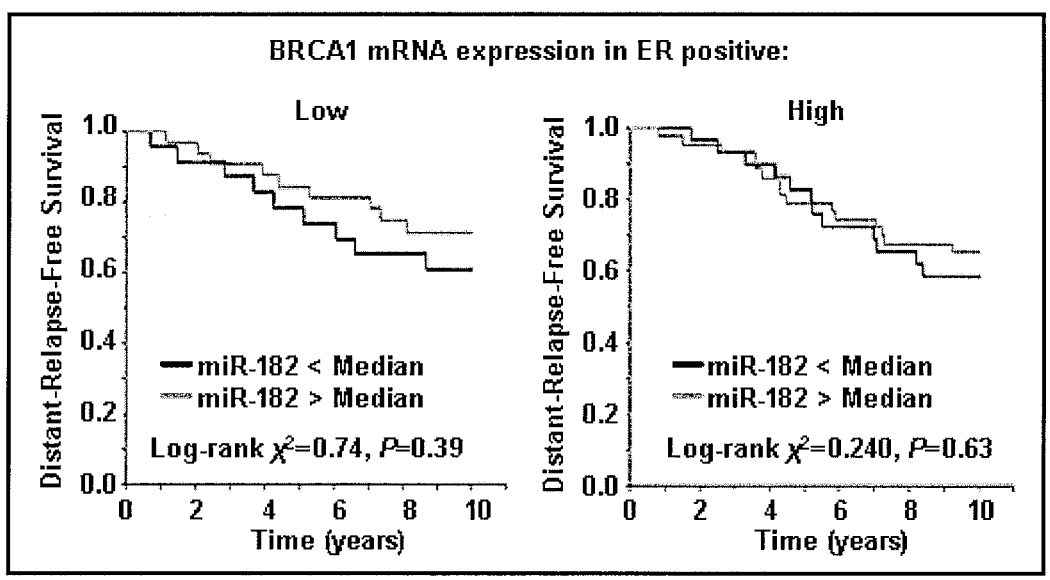
FIG. 20 depicts Kaplan-Meier plots that show that miR-182 expression does not correlate with DRFS in ER-positive breast tumors. ER-positive tumors studied included tumors from 55 patients with low BRCA1 median mRNA expression (left panel) and 72 patients with high BRCA1 median mRNA expression (right panel).

Patients with ER-positive tumors classified by BRCA1 expression did not show any correlation between miR-182 expression and survival (FIG. 20).

These data clearly suggest that miR-182 expression is clinically relevant in ER-negative tumors when co-expressed with BRCA1 mRNA.

Example 14 miR-182 Downregulates BRCA1 in ER-Negative Breast Tumors

To address whether the impact of miR-182 on survival was due to regulation of BRCA1, BRCA1 protein levels in primary breast tumors were assessed by immunohistochemistry (IHC, FIGS. 18C, D). Representative images of tumors, including a BRCA1 mutant sample as a negative control, are shown (FIG. 18C). Since all patients are not routinely tested for BRCA mutation status, the BRCA1 mutation status of all the tumors analyzed in this tissue microarray were not available. Tumors that showed no BRCA1 staining were deliberately excluded from the analysis because they were likely to represent patients with BRCA1 mutations/deletions. Classifying the tumors into high BRCA1 protein levels and low/medium BRCA1 levels, the potential correlation with miR-182 expression was analyzed. Consistent with the data in ER-negative tumor cell lines, there was a statistically significant inverse correlation of BRCA1 protein and miR-182 in these tumors (FIG. 18D). These clinical observations show that miR-182 downregulates BRCA1 in ER-negative breast tumors.

What is claimed is:

1. A method comprising steps in the following order:
   (a) providing a sample from a cancer patient;
   (b) measuring a level of miR-182 in the sample;
   (c) identifying the cancer patient as a suitable candidate for treatment with the PARP inhibitor if the level of miR-182 in the sample is higher than a level of miR-182 in a control sample and
   identifying the cancer patient as an unsuitable candidate for treatment with the PARP inhibitor if the level of miR-182 in the sample is lower than a level of miR-182 in a control sample; and
   (d) administering the PARP inhibitor to the cancer patient identified as the suitable candidate, and not administering the PARP inhibitor to the cancer patient that is identified as the unsuitable candidate.

2. The method of claim 1, wherein the patient has a cancer selected from the group consisting of breast cancer, ovarian cancer, prostate cancer, bladder cancer, testicular cancer, cervical cancer, uterine cancer, pancreatic cancer, melanoma, and colon cancer.

3. The method of claim 2, wherein the patient has breast cancer.

4. The method of claim 2, wherein the patient has ovarian cancer.

5. The method of claim 1, wherein the sample is a biopsy sample from a cancerous breast of the patient.

6. The method of claim 1, wherein the sample is a biopsy sample from an ovary of the patient.

7. A method comprising steps in the following order:
(a) providing a sample from a cancer patient;
(b) measuring a level of miR-182 in one or more cells in the sample;
(c) identifying the cancer patient as a suitable candidate for treatment with an agent that can be effective against cancers expressing a low level of BRCA1 if the level of miR-182 in the sample is higher than a level of miR-182 in a control sample and
identifying the cancer patient as an unsuitable candidate for treatment with an agent that can be effective against cancers expressing a low level of BRCA1 if the level of miR-182 in the sample is lower than a level of miR-182 in a control sample; and
(d) administering the agent that can be effective against cancers expressing a low level of BRCA1 to the cancer patient identified as the suitable candidate, and not administering the agent that can be effective against cancers expressing a low level of BRCA1 to the cancer patient that is identified as the unsuitable candidate,
wherein the agent that can be effective against cancers expressing a low level of BRCA1 is a chemotherapeutic agent selected from the group consisting of an alkylating agent, a topoisomerase inhibitor, an antimetabolite, an anthracycline, an antitumor antibiotic, and an epipodophyllotoxin.

8. The method of claim 7, wherein the chemotherapeutic agent is a topoisomerase inhibitor, an anthracycline, or an epipodophyllotoxin.

9. The method of claim 1, wherein the PARP inhibitor is selected from the group consisting of 4-Amino-1, 8-naphthalimide (ANI), ABT-888, KU59436, AZD2281/Olaparib, AG014699, BSI-201, INO-1001, and GPI 21016.

10. A method comprising steps in the following order:
(a) providing a sample from a cancer patient;
(b) measuring a level of miR-182 in one or more cells in the sample;
(c) identifying the cancer patient as a suitable candidate for treatment with an agent that can be effective against cancers expressing a high level of BRCA1 if the level of miR-182 in the sample is lower than a level of miR-182 in a control sample and
identifying the cancer patient as an unsuitable candidate for treatment with an agent that can be effective against cancers expressing a high level of BRCA1 if the level of miR-182 in the sample is higher than a level of miR-182 in a control sample; and
(d) administering the agent that can be effective against cancers expressing a high level of BRCA1 to the cancer patient identified as the suitable candidate, and not administering the agent that can be effective against cancers expressing a high level of BRCA1 to the cancer patient that is identified as the unsuitable candidate.

11. The method of claim 10, wherein the agent that can be effective against cancers expressing a high level of BRCA1 is a spindle toxin.

12. The method of claim 11, wherein the spindle toxin is selected from the group consisting of taxanes and *vinca* alkaloids.

13. The method of claim 11, wherein the spindle toxin is selected from the group consisting of paclitaxel, vincristine, vinblastine, vinorelbine, and vindesine.

14. The method of claim 1, wherein the sample is a biopsy sample or a blood sample.

15. The method of claim 7, wherein the sample is a biopsy sample or a blood sample.

16. The method of claim 10, wherein the sample is a biopsy sample or a blood sample.

17. The method of claim 1, wherein measuring a level of miRNA-182 comprises quantitative or semi-quantitative PCR.

18. The method of claim 7, wherein measuring a level of miRNA-182 comprises quantitative or semi-quantitative PCR.

19. The method of claim 10, wherein measuring a level of miRNA-182 comprises quantitative or semi-quantitative PCR.

20. The method of claim 1, wherein measuring a level of miRNA-182 comprises qualitative, quantitative, or semi-quantitative in situ hybridization.

21. The method of claim 7, wherein measuring a level of miRNA-182 comprises qualitative, quantitative, or semi-quantitative in situ hybridization.

22. The method of claim 10, wherein measuring a level of miRNA-182 comprises qualitative, quantitative, or semi-quantitative in situ hybridization.

* * * * *

UNITED STATES PATENT AND TRADEMARK OFFICE
CERTIFICATE OF CORRECTION

Page 1 of 1

PATENT NO. : 9,642,821 B2
APPLICATION NO. : 13/005899
DATED : May 9, 2017
INVENTOR(S) : Chowdhury It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 725 days.

Signed and Sealed this
Seventeenth Day of October, 2017

Joseph Matal
*Performing the Functions and Duties of the
Under Secretary of Commerce for Intellectual Property and
Director of the United States Patent and Trademark Office*

SEQUENCE LISTING

<160> NUMBER OF SEQ ID NOS: 46

<210> SEQ ID NO 1
<211> LENGTH: 24
<212> TYPE: RNA
<213> ORGANISM: Homo sapiens

<400> SEQUENCE: 1
uuuggcaaug guagaacuca cacu                                              24

<210> SEQ ID NO 2
<211> LENGTH: 9
<212> TYPE: RNA
<213> ORGANISM: Homo sapiens

```
<400> SEQUENCE: 2 uuuggcaau                                                               9

<210> SEQ ID NO 3
<211> LENGTH: 15
<212> TYPE: RNA
<213> ORGANISM: Homo sapiens

<400> SEQUENCE: 3
gguagaacuc acacu                                                       15

<210> SEQ ID NO 4
<211> LENGTH: 1381
<212> TYPE: DNA
<213> ORGANISM: Homo sapiens

<400> SEQUENCE: 4
ctgcagccag ccacaggtac agagccacag gacccccaaga atgagcttac aaagtggcct      60
ttccaggccc tgggagctcc tctcactctt cagtccttct actgtcctgg ctactaaata     120
ttttatgtac atcagcctga aaaggacttc tggctatgca agggtcccctt aaagattttc    180 tgcttgaagt ctcccttgga aatctgccat gagcacaaaa ttatggtaat ttttcacctg     240
agaagatttt aaaaccattt aaacgccacc aattgagcaa gatgctgatt cattatttat     300 cagcccctatt ctttctattc aggctgttgt tggcttaggg ctgaagcac agagtggctt     360 ggcctcaaga gaatagctgg tttcccctaag tttacttctc taaaaccctg tgttcacaaa    420
ggcagagagt cagacccttc aatggaagga gagtgcttgg gatcgattat gtgacttaaa    480
gtcagaatag tccttgggca gttctcaaat gttggagtgg aacattgggg aggaaattct    540
gaggcaggta ttagaaatga aaaggaaact tgaaacctgg gcatggtggc tcacgcctgt    600
aatcccagca ctttgggagg ccaaggtggg cagatcactg gaggtcagga gttcgaaacc    660
agcctggcca acatggtgaa acccccatctc tactaaaaat acagaaatta gccggtcatg    720
gtggtggaca cctgtaatcc cagctactca ggtggctaag gcaggagaat cacttcagcc    780
cgggaggtgg aggttgcagt gagccaagat cataccacgg cactccagcc tgggtgacag    840
tgagactgtg gctcaaaaaa aaaaaaaaa aaggaaaat gaaactagaa gagatttcta     900
aaagtctgag atatatttgc tagatttcta aagaatgtgt tctaaaacag cagaagatt     960 tcaagaaccg gtttccaaag acagtcttct aattcctcat tagtaataag taaaatgttt   1020
attgttgtag ctctggtata taatccattc ctcttaaaat ataagacctc tggcatgaat    1080
atttcatatc tataaaatga cagatcccac caggaaggaa gctgttgctt tctttgaggt    1140 gattttttc ctttgctccc tgttgctgaa accatacagc ttcataaata attttgcttg    1200
ctgaaggaag aaaaagtgtt tttcataaac ccattatcca ggactgttta tagctgttgg   1260
aaggactagg tcttccctag ccccccccagt gtgcaagggc agtgaagact tgattgtaca   1320
aaatacgttt tgtaaatgtt gtgctgttaa cactgcaaat aaacttggta gcaaacactt   1380
c                                                                  1381

<210> SEQ ID NO 5
<211> LENGTH: 24
<212> TYPE: RNA
<213> ORGANISM: Homo sapiens

<400> SEQUENCE: 5
augaaacuag aagagauuuc uaaa                                              24
```

-continued

```
<210> SEQ ID NO 6
<211> LENGTH: 24
<212> TYPE: RNA
<213> ORGANISM: Homo sapiens

<400> SEQUENCE: 6
agauauauuu gcuagauuuc uaaa                                              24

<210> SEQ ID NO 7
<211> LENGTH: 24
<212> TYPE: RNA
<213> ORGANISM: Homo sapiens

<400> SEQUENCE: 7
cuaaaacagc agaagauuuu caag                                              24

<210> SEQ ID NO 8
<211> LENGTH: 24
<212> TYPE: RNA
<213> ORGANISM: Homo sapiens

<400> SEQUENCE: 8
gauuuucaag aaccgguuuc caaa                                              24

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
caacatgccc acagatcaac                                                   20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
atggaagcca ttgtcctctg                                                   20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
agtgccaagt gagggagcta                                                   20

<210> SEQ ID NO 12
<211> LENGTH: 19
<212> TYPE: DNA
<213> ORGANISM: Artificial Sequence
<220> FEATURE:
<223> OTHER INFORMATION: oligonucleotide

<400> SEQUENCE: 12
ccacttggac ctcttgtgt                                                    19
```

```
<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
gataagggcg acagcaacag                                                   20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
ccagttccct cattctggac                                                   20

<210> SEQ ID NO 15
<211> LENGTH: 19
<212> TYPE: DNA
<213> ORGANISM: Artificial Sequence
<220> FEATURE:
<223> OTHER INFORMATION: oligonucleotide

<400> SEQUENCE: 15
gcccgatctc gtctgatct                                                    19

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
agcctacagc acccggtatt                                                   20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
tgcaccacca actgcttagc                                                   20

<210> SEQ ID NO 18
<211> LENGTH: 21
<212> TYPE: DNA
<213> ORGANISM: Artificial Sequence
<220> FEATURE:
<223> OTHER INFORMATION: oligonucleotide

<400> SEQUENCE: 18
ggcatggact gtggtcatga g                                                 21

<210> SEQ ID NO 19
<211> LENGTH: 20
<212> TYPE: DNA
<213> ORGANISM: Artificial Sequence
<220> FEATURE:
<223> OTHER INFORMATION: oligonucleotide
```

```
<400> SEQUENCE: 19
cttggagctg gtcctttcag                                              20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
ccttccccag cttcattaca                                              20

<210> SEQ ID NO 21
<211> LENGTH: 30
<212> TYPE: DNA
<213> ORGANISM: Artificial Sequence
<220> FEATURE:
<223> OTHER INFORMATION: oligonucleotide

<400> SEQUENCE: 21
cggcggccgc gatatgaggg gaagggagga                                   30

<210> SEQ ID NO 22
<211> LENGTH: 30
<212> TYPE: DNA
<213> ORGANISM: Artificial Sequence
<220> FEATURE:
<223> OTHER INFORMATION: oligonucleotide

<400> SEQUENCE: 22
cggcggccgc gagaaggttc accacccaga                                   30

<210> SEQ ID NO 23
<211> LENGTH: 29
<212> TYPE: DNA
<213> ORGANISM: Artificial Sequence
<220> FEATURE:
<223> OTHER INFORMATION: oligonucleotide

<400> SEQUENCE: 23
ataagcttca ttggaagagc caccacttc                                    29

<210> SEQ ID NO 24
<211> LENGTH: 28
<212> TYPE: DNA
<213> ORGANISM: Artificial Sequence
<220> FEATURE:
<223> OTHER INFORMATION: oligonucleotide

<400> SEQUENCE: 24
actcgagttg cttggcttga attattgg                                     28

<210> SEQ ID NO 25
<211> LENGTH: 103
<212> TYPE: DNA
<213> ORGANISM: Artificial Sequence
<220> FEATURE:
<223> OTHER INFORMATION: oligonucleotide

<400> SEQUENCE: 25
ctagtagaag agatttctaa aagtctgaga tatatttgct agatttctaa agaatgtgtt   60
ctaaaacagc agaagatttt caagaaccgg tttccaaaga cag                   103
```

```
<210> SEQ ID NO 26
<211> LENGTH: 100
<212> TYPE: DNA
<213> ORGANISM: Artificial Sequence
<220> FEATURE:
<223> OTHER INFORMATION: oligonucleotide

<400> SEQUENCE: 26
agctctgtct ttggaaaccg gttcttgaaa atcttctgct gttttagaac acattcttta      60
gaaatctagc aaatatatct cagactttta gaaatctctt                           100

<210> SEQ ID NO 27
<211> LENGTH: 99
<212> TYPE: DNA
<213> ORGANISM: Artificial Sequence
<220> FEATURE:
<223> OTHER INFORMATION: oligonucleotide

<400> SEQUENCE: 27
ctagaagaga cgatacccgt ctgagatata tttgctaggc gataccgggg tgtgttctaa      60
aacagcagaa gccgataccc ggccggcgat acccgacag                             99

<210> SEQ ID NO 28
<211> LENGTH: 103
<212> TYPE: DNA
<213> ORGANISM: Artificial Sequence
<220> FEATURE:
<223> OTHER INFORMATION: oligonucleotide

<400> SEQUENCE: 28
agctctgtcg ggtatcgccg gccgggtatc gcttctgctg ttttagaaca cacccgggta      60
tcgcctagca aatatatctc agacgggtat cgctctcttc tag                       103

<210> SEQ ID NO 29
<211> LENGTH: 29
<212> TYPE: RNA
<213> ORGANISM: Homo sapiens

<400> SEQUENCE: 29
ccguuuuugg caaugguaga acucacacu                                        29

<210> SEQ ID NO 30
<211> LENGTH: 28
<212> TYPE: RNA
<213> ORGANISM: Homo sapiens

<400> SEQUENCE: 30
cgauuuuggc acuagcacau uuuugcuu                                         28

<210> SEQ ID NO 31
<211> LENGTH: 25
<212> TYPE: RNA
<213> ORGANISM: Homo sapiens

<400> SEQUENCE: 31
guauggcacu gguagaauuc acugu                                            25

<210> SEQ ID NO 32
<211> LENGTH: 29
<212> TYPE: RNA
<213> ORGANISM: Pan troglodytes

<400> SEQUENCE: 32
```

-continued

```
ccguuuuugg caaugguaga acucacacu                                      29

<210> SEQ ID NO 33
<211> LENGTH: 28
<212> TYPE: RNA
<213> ORGANISM: Pan troglodytes

<400> SEQUENCE: 33
cgauuuuggc acuagcacau uuuugcuu                                       28

<210> SEQ ID NO 34
<211> LENGTH: 25
<212> TYPE: RNA
<213> ORGANISM: Pan troglodytes

<400> SEQUENCE: 34
guauggcacu gguagaauuc acugu                                          25

<210> SEQ ID NO 35
<211> LENGTH: 29
<212> TYPE: RNA
<213> ORGANISM: Macaca mulatta

<400> SEQUENCE: 35
cuguuuuugg caaugguaga acucacacu                                      29

<210> SEQ ID NO 36
<211> LENGTH: 28
<212> TYPE: RNA
<213> ORGANISM: Macaca mulatta

<400> SEQUENCE: 36
cgauuuuggc acuagcacau uuuugcuu                                       28

<210> SEQ ID NO 37
<211> LENGTH: 25
<212> TYPE: RNA
<213> ORGANISM: Macaca mulatta

<400> SEQUENCE: 37
guauggcacu gguagaauuc acugu                                          25

<210> SEQ ID NO 38
<211> LENGTH: 29
<212> TYPE: RNA
<213> ORGANISM: Mus musculus

<400> SEQUENCE: 38
ccauuuuugg caaugguaga acucacacc                                      29

<210> SEQ ID NO 39
<211> LENGTH: 28
<212> TYPE: RNA
<213> ORGANISM: Mus musculus

<400> SEQUENCE: 39
cgauuuuggc acuagcacau uuuugcuu                                       28

<210> SEQ ID NO 40
<211> LENGTH: 25
<212> TYPE: RNA
<213> ORGANISM: Mus musculus
```

```
<400> SEQUENCE: 40
guauggcacu gguagaauuc acugu                                          25

<210> SEQ ID NO 41
<211> LENGTH: 29
<212> TYPE: RNA
<213> ORGANISM: Xenopus tropicalis

<400> SEQUENCE: 41
caguguuugg caaugguaga acucacacu                                      29

<210> SEQ ID NO 42
<211> LENGTH: 28
<212> TYPE: RNA
<213> ORGANISM: Xenopus tropicalis

<400> SEQUENCE: 42
cugcuuuggc acuagcacau uuuugcuu                                       28

<210> SEQ ID NO 43
<211> LENGTH: 25
<212> TYPE: RNA
<213> ORGANISM: Xenopus tropicalis

<400> SEQUENCE: 43
guauggcacu gguagaauuc acugu                                          25

<210> SEQ ID NO 44
<211> LENGTH: 9
<212> TYPE: RNA
<213> ORGANISM: Homo sapiens

<400> SEQUENCE: 44 auuucuaaa                                                             9

<210> SEQ ID NO 45
<211> LENGTH: 9
<212> TYPE: RNA
<213> ORGANISM: Homo sapiens

<400> SEQUENCE: 45 auuuucaag                                                             9

<210> SEQ ID NO 46
<211> LENGTH: 9
<212> TYPE: RNA
<213> ORGANISM: Homo sapiens

<400> SEQUENCE: 46 guuuccaaa                                                             9
```